United States Patent
Everman et al.

(10) Patent No.: US 11,911,158 B2
(45) Date of Patent: Feb. 27, 2024

(54) SYSTEMS AND METHODS FOR DETERMINING ACTOR STATUS ACCORDING TO BEHAVIORAL PHENOMENA

(71) Applicant: GMECI, LLC, Beavercreek, OH (US)

(72) Inventors: Bradford R. Everman, Haddonfield, NJ (US); Brian Scott Bradke, Brookfield, VT (US)

(*) Notice: Subject to any disclaimer, the term of this patent is extended or adjusted under 35 U.S.C. 154(b) by 0 days.

(21) Appl. No.: 18/127,998

(22) Filed: Mar. 29, 2023

(65) Prior Publication Data

US 2023/0346278 A1    Nov. 2, 2023

Related U.S. Application Data

(63) Continuation of application No. 18/093,872, filed on Jan. 6, 2023, which is a continuation of application (Continued)

(51) Int. Cl.
| | | |
|---|---|---|
| *A61B 5/16* | (2006.01) | |
| *A61B 5/00* | (2006.01) | |
| *G10L 15/06* | (2013.01) | |
| *G10L 15/22* | (2006.01) | |
| *G10L 25/63* | (2013.01) | |

(52) U.S. Cl.
CPC .............. *A61B 5/165* (2013.01); *A61B 5/163* (2017.08); *A61B 5/4803* (2013.01); *A61B 5/7221* (2013.01); *A61B 5/7267* (2013.01); *G10L 15/063* (2013.01); *G10L 15/22* (2013.01); *G10L 25/63* (2013.01)

(58) Field of Classification Search
CPC ....... A61B 5/163; A61B 5/165; A61B 5/4803; A61B 5/7221; A61B 5/7267
See application file for complete search history.

(56) References Cited

U.S. PATENT DOCUMENTS

| | | |
|---|---|---|
| H1039 H | 4/1992 | Tripp, Jr. et al. |
| 6,032,065 A | 2/2000 | Brown |
| (Continued) | | |

FOREIGN PATENT DOCUMENTS

| | | |
|---|---|---|
| WO | 2018096335 | 5/2018 |
| WO | 2021050950 | 3/2021 |

OTHER PUBLICATIONS

N/A, Cobham VigilOX™ Pilot Breathing Sensors Fly on F-18 and T-45, Jul. 16, 2018.
N/A, Insta Pilot's Breath Air Monitor, Apr. 7, 2021.

*Primary Examiner* — Brian T Gedeon
(74) *Attorney, Agent, or Firm* — Caldwell Intellectual Property Law

(57) ABSTRACT

Aspects relate to systems and methods for determining actor status according to behavioral phenomena. An exemplary system includes at least an eye sensor, wherein the at least an eye sensor is configured to detect an eye parameter and at least a physiological sensor, wherein the at least a physiological sensor is configured to detect a circulatory parameter, and a processor in communication with the at least an eye speech sensor and the at least a physiological sensor and configured to determine an eye pattern as a function of the eye parameter and correlate the eye pattern and the circulatory parameter to a cognitive status.

20 Claims, 14 Drawing Sheets

Related U.S. Application Data

No. 17/731,935, filed on Apr. 28, 2022, now Pat. No. 11,596,334.

(56) References Cited

U.S. PATENT DOCUMENTS

| | | |
|---|---|---|
| 8,281,787 B2 | 10/2012 | Burton |
| 9,950,201 B2 | 4/2018 | Zimmerman et al. |
| 10,182,787 B2 | 1/2019 | De Waele et al. |
| 10,419,053 B2 | 9/2019 | Ruttler et al. |
| 10,786,693 B1 | 9/2020 | Opperman et al. |
| 10,874,346 B1 | 12/2020 | Lisy et al. |
| 2010/0217097 A1* | 8/2010 | Chen ................... G16H 50/20 600/300 |
| 2010/0274102 A1 | 10/2010 | Teixeira |
| 2020/0405215 A1* | 12/2020 | Tinjust ................ A61B 5/7405 |

* cited by examiner

SYSTEMS AND METHODS FOR DETERMINING ACTOR STATUS ACCORDING TO BEHAVIORAL PHENOMENA

CROSS-REFERENCE TO RELATED APPLICATIONS

This application is a continuation of Non-provisional application Ser. No. 18/093,872, filed on Jan. 6, 2023, and entitled "SYSTEMS AND METHODS FOR DETERMINING ACTOR STATUS ACCORDING TO BEHAVIORAL PHENOMENA," which is a continuation of Non-provisional application Ser. No. 17/731,935 filed on Apr. 28, 2022 and entitled "SYSTEMS AND METHODS FOR DETERMINING ACTOR STATUS ACCORDING TO BEHAVIORAL PHENOMENA," the entirety of each of which is incorporated herein by reference.

FIELD OF THE INVENTION

The present invention generally relates to the field of diagnosing human conditions. In particular, the present invention is directed to systems and methods for determining actor status according to behavioral phenomena.

BACKGROUND

Poor cognitive states of an actor can hobble performance of high stress and/or high stakes responsibilities. Poor performance can result in unacceptable outcomes, such as loss of casualties, loss of life, and loss of assets.

SUMMARY OF THE DISCLOSURE

In an aspect, a system for determining actor status according to behavioral phenomenon is described. The system includes at least an eye sensor, wherein the at least an eye sensor is configured to detect an eye parameter and at least a physiological sensor, wherein the at least a physiological sensor is configured to detect a circulatory parameter. The system further including a processor in communication with the at least an eye sensor and the at least a physiological sensor and configured to receive the eye parameter and the circulatory parameter, determine an eye pattern as a function of the eye parameter; and correlate the eye pattern and the circulatory parameter to a cognitive status. Correlating the eye pattern and the circulatory parameter to the cognitive status includes receiving cognitive status training data including behavioral parameters correlated to a plurality of cognitive statuses, wherein the behavioral parameters comprise a plurality of circulatory parameters and a plurality of eye patterns, training a cognitive status machine learning model as a function of the cognitive status training data, and determining the cognitive status as a function of the cognitive status machine learning model, the eye pattern, and the circulatory parameter.

In another aspect, a method for determining actor status according to behavioral phenomenon is described. the method includes detecting, by at least an eye sensor, an eye parameter, detecting, by at least a physiological sensor, a circulatory parameter, receiving, by a processor, the eye parameter and the circulatory parameter, determining, by the processor, an eye pattern as a function of the eye parameter, and correlating, by the processor, the eye pattern and the circulatory parameter to a cognitive status. Correlating the eye pattern and the circulatory parameter to the cognitive status includes receiving cognitive status training data including behavioral parameters correlated to a plurality of cognitive statuses, wherein the behavioral parameters comprise a plurality of circulatory parameters and a plurality of eye patterns, training a cognitive status machine learning model as a function of the cognitive status training data, and determining the cognitive status as a function of the cognitive status machine learning model, the eye pattern, and the circulatory parameter.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining actor status according to behavioral phenomenon. In an embodiment, an actor may include a pilot, such as a fighter pilot.

Aspects of the present disclosure can be used to ascertain a level of cognitive ability of a person, as a function of objective phenomena associated with their behavior. Aspects of the present disclosure can also be used to track cognitive ability over time for one or more actors. This is so, at least in part, because an actor's cognitive status is likely change, for instance according to a number of variables, including without limitation levels of rest, levels of hunger, and the like.

Exemplary embodiments illustrating aspects of the present disclosure are described below in the context of several specific examples.

Figure 1:
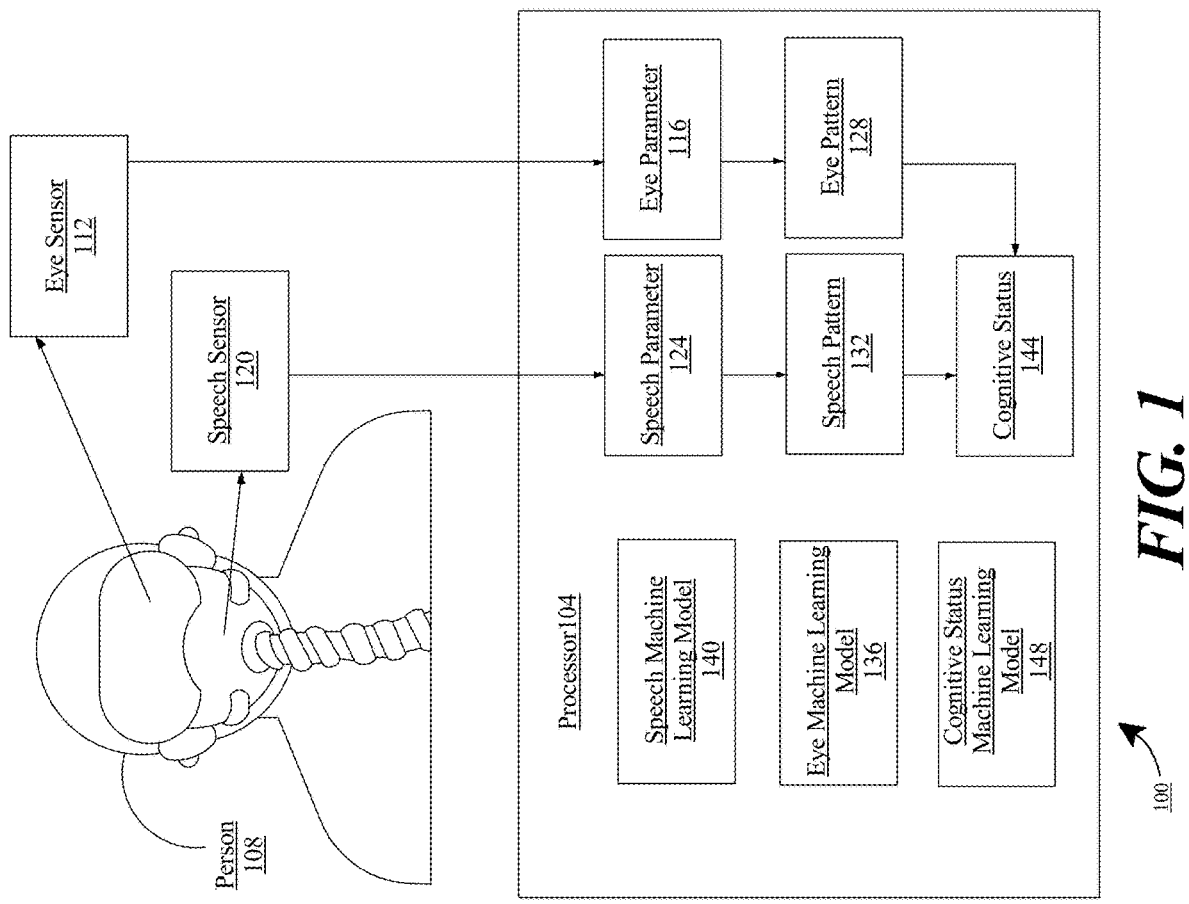
FIG. 1 is a block diagram illustrating an exemplary system for determining actor status according to behavioral phenomena.

Referring now to FIG. 1, an exemplary embodiment of a system 100 for determining a status according to behavioral phenomenon is illustrated. In some cases, status may include an actor status. An "actor," as used in this disclosure, is one who is, at any point in time, engaged in an action and/or responsibility of relative importance. An exemplary actor includes a pilot, who is presently or may in the future be engaged in an important task of flying an airplane. In some cases, status may include a pilot status. As used in this disclosure, "pilot status" is a behavioral or cognitive status of a pilot. As used in this disclosure, "behavioral phenomena" are observable physiological phenomena associated with conscious or unconscious actions of a person. Exemplary non-limiting behavioral phenomenon include eye phenomenon, as represented by eye parameters and eye patterns, speech phenomenon, as represented by speech parameters and speech patterns, and the like. System 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of system 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 may determine a status of a person 108. In some cases, person 108 may be an operator of equipment. In some cases, person's 108 task may be physically and/or cognitively challenging as well as "high stakes." For instance, in some cases consequences of a person's under-performance may be very high and result in substantial loss of equipment and/or life. An exemplary such person 108 is a pilot 108, for example a fighter pilot 108.

With continued reference to FIG. 1, system 100 may include at least an eye sensor 112. As used in this disclosure, an "eye sensor" is any system or device that is configured or adapted to detect an eye parameter as a function of an eye phenomenon. In some cases, at least an eye sensor 112 may be configured to detect at least an eye parameter 116 as a function of at least an eye phenomenon. As used in this disclosure, an "eye parameter" is an element of information associated with an eye. Exemplary non-limiting eye parameters may include blink rate, eye-tracking parameters, pupil location, gaze directions, pupil dilation, and the like. Exemplary eye parameters are described in greater detail below. In some cases, an eye parameter 116 may be transmitted or represented by an eye signal. An eye signal may include any signal described in this disclosure. As used in this disclosure, an "eye phenomenon" may include any observable phenomenon associated with an eye, including without limitation focusing, blinking, eye-movement, and the like. Eye sensor 112 may include any sensor described in this disclosure, including with reference to FIG. 2 below. In some embodiments, at least an eye sensor 112 may include an electromyography sensor 112. Electromyography sensor may be configured to detect at least an eye parameter 116 as a function of at least an eye phenomenon.

Still referring to FIG. 1, in some embodiments, eye sensor 112 may include an optical eye sensor 112. Optical eye sensor 112 may be configured to detect at least an eye parameter 116 as a function of at least an eye phenomenon. In some cases, an optical eye sensor 112 may include a camera directed toward one or both of person's 108 eyes. In some cases, optical eye sensor 112 may include a light source, likewise directed to person's 108 eyes. Light source may have a non-visible wavelength, for instance infrared or near-infrared. In some cases, a wavelength may be selected which reflects at an eye's pupil (e.g., infrared). Light that selectively reflects at an eye's pupil may be detected, for instance by camera. Images 116 of eyes may be captured by camera 112. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object (e.g., person 108 or person's eyes). In some cases, image data 116 may be generated by a camera. "Image data" may be used interchangeably through this disclosure with "image," where image 116 is used as a noun. An image 116 may be optical, such as without limitation where at least an optic is used to generate an image 116 of an object 108. An image 116 may be material, such as without limitation when film is used to capture an image 116. An image 116 may be digital, such as without limitation when represented as a bitmap. Alternatively, an image 116 may be comprised of any media capable of representing a physical scene, space, and/or object 108. Alternatively where "image" is used as a verb, in this disclosure, it refers to generation and/or formation of an image 116.

Still referring to FIG. 1, an exemplary camera 112 is an OpenMV Cam H7 from OpenMV, LLC of Atlanta, Georgia, U.S.A. OpenMV Cam includes a small, low power, microcontroller 104 which allows execution of processes. OpenMV Cam comprises an ARM Cortex M7 processor 104 and a 640×480 image sensor 112 operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detect motion, for example by way of frame differencing algorithms; detect markers, for example blob detection; detect objects, for example face detection; track eyes; detection persons, for example by way of a trained machine learning model; detect camera motion, for example by way of optical flow detection; detect and decode barcodes; capture images; and record video.

Still referring to FIG. 1, in some cases, a camera 112 may be used to determine eye patterns 128 (e.g., track eye movements). For instance, camera 112 may capture images 116 and processor 104 (internal or external) to camera may process images 116 to track eye movements 128. In some embodiments, a video-based eye tracker may use corneal reflection (e.g., first Purkinje image) and a center of pupil as features to track over time. A more sensitive type of eye-tracker, a dual-Purkinje eye tracker, may use reflections from a front of cornea (i.e., first Purkinje image) and back of lens (i.e., fourth Purkinje image) as features to track. A still more sensitive method of tracking may include use of image features from inside eye, such as retinal blood vessels, and follow these features as the eye rotates. In some cases, optical methods, particularly those based on video recording, may be used for gaze-tracking and may be non-invasive and inexpensive.

For instance, in some cases a relative position between camera 112 and person 108 may be known or estimable. Pupil location may be determined through analysis of images (either visible or infrared images). In some cases, camera 112 may focus on one or both eyes and record eye movement as viewer 108 looks. In some cases, eye-tracker 112 may use center of pupil and infrared/near-infrared non-collimated light to create corneal reflections (CR). A vector between pupil center and corneal reflections can be used to compute a point of regard on surface (i.e., a gaze direction). In some cases, a simple calibration procedure with an individual person 108 may be needed before using an optical eye tracker 112. In some cases, two general types of infrared/near-infrared (also known as active light) eye-tracking techniques can be used: bright-pupil (light reflected by pupil) and dark-pupil (light not reflected by pupil). Difference between bright-pupil and dark pupil images 116 may be based on a location of illumination source with respect to optics. For instance, if illumination is coaxial with optical path, then eye may act as a retroreflector as the light reflects off retina creating a bright pupil effect similar to red eye. If illumination source is offset from optical path, then pupil may appear dark because reflection from retina is directed away from camera 112. In some cases, bright-pupil tracking creates greater iris/pupil contrast, allowing more robust eye-tracking with all iris pigmentation, and greatly reduces interference caused by eyelashes and other obscuring features. In some cases, bright-pupil tracking may also allow tracking in lighting conditions ranging from total darkness to very bright.

Still referring to FIG. 1, alternatively, in some cases, a passive light optical eye tracking method may be employed. Passive light optical eye tracking may use visible light to illuminate. In some cases, passive light optical tracking yields less contrast of pupil than with active light methods; therefore, in some cases, a center of iris may be used for calculating a gaze vector. In some cases, a center of iris determination requires detection of a boundary of iris and sclera (e.g., limbus tracking). In some case, eyelid obstruction of iris and our sclera may challenge calculations of an iris center.

Still referring to FIG. 1, some optical eye tracking systems may be head-mounted, some may require the head to be stable, and some may function remotely and automatically track the head during motion. Optical eye tracking systems 112 may capture images 116 at frame rate. Exemplary frame rates include 15, 30, 60, 120, 240, 350, 1000, and 1250 Hz.

With continued reference to FIG. 1, system may include at least a speech sensor 120. As used in this disclosure, a "speech sensor" is any system or device that is configured or adapted to detect a speech parameter as a function of a speech phenomenon. In some cases, speech sensor 120 may be configured to detect at least a speech parameter 124 as a function of at least a speech phenomenon. As used in this disclosure, a "speech parameter" is an element of information associated with speech. An exemplary non-limiting speech parameter is a representation of at least a portion of audible speech, for instance a digital representation of audible speech. In some cases, a speech parameter 124 may be transmitted or represented by a speech signal. A speech signal may include any signal described in this disclosure. As used in this disclosure, a "speech phenomenon" may include any observable phenomenon associated with speech, including without limitation audible phenomena and/or acoustic phenomena. Speech phenomena may include pressure changes, for instance audible pressure changes as detectable by a microphone. In some cases, speech phenomenon may not be directly related to speech, and may include phenomena related to breathing. For example, breathing sounds may be detected by speech sensor 120 and used as speech parameter 124. Speech sensor 120 may include any sensor described in this disclosure, including with reference to FIGS. 3A-3E below. In some embodiments, at least a speech sensor 120 may include a bone conductance transducer 120. In some cases, bone conductance transducer 120 may be configured to detect at least a speech parameter 124 as a function of at least a speech phenomenon, see FIGS. 3A-3E. In some cases, system 100 may utilize communication signals and use them as representation of speech parameters 124. For instance, in some cases, a person 108 may already be in audible communication with others, through communication microphones. These communication signals may be used by system 100 as speech parameters 124.

Still referring to FIG. 1, in some cases, speech sensor 120 may include a microphone, for example an air spaced microphone. In some cases, microphone 120 may be configured to detect at least a speech parameter 124 as a function of at least a speech phenomenon. In some cases, speech phenomenon may include sound or sounds associated with speech, i.e., oral verbalization. As used in this disclosure, a "microphone" is any transducer configured to transduce pressure change phenomenon to a signal, for instance a signal representative of a parameter associated with the phenomenon. Microphone, according to some embodiments, may include a transducer configured to convert sound into an audio signal. Exemplary non-limiting microphones include dynamic microphones (which may include a coil of wire suspended in a magnetic field), condenser microphones (which may include a vibrating diaphragm condensing plate), and a contact (or conductance) microphone (which may include piezoelectric crystal material). Microphone 120 may include any microphone for transducing pressure changes, as described above; therefore, microphone 120 may include any variety of microphone, including any of: condenser microphones, electret microphones, dynamic microphones, ribbon microphones, carbon microphones, piezoelectric microphones, fiber-optic microphones, laser microphones, liquid microphones, microelectromechanical systems (MEMS) microphones, and/or a speaker microphone. An "audio signal," as used in this disclosure, is a representation of sound. In some cases, an audio signal may include an analog electrical signal of time-varying electrical potential. In some embodiments, an audio signal may be communicated (e.g., transmitted and/or received) by way of an electrically transmissive path (e.g., conductive wire), for instance an audio signal path. Alternatively or additionally, audio signal may include a digital signal of time-varying digital numbers. In some cases, a digital audio signal may be communicated (e.g., transmitted and/or received) by way of any of an optical fiber, at least an electrically transmissive path, and the like. In some cases, a line code and/or a communication protocol may be used to aid in communication of a digital audio signal. Exemplary digital audio transports include, without limitation, Alesis Digital Audio Tape (ADAT), Tascam Digital Interface (TDIF), Toshiba Link (TOSLINK), Sony/Philips Digital Interface (S/PDIF), Audio Engineering Society standard 3 (AES3), Multichannel Audio Digital Interface (MADI), Musical Instrument Digital Interface (MIDI), audio over Ethernet, and audio over IP. Audio signals may represent frequencies within an audible range corresponding to ordinary limits of human hearing, for example substantially between about 20 and about 20,000 Hz. According to some embodiments, an audio signal may include one or more parameters, such as without limitation bandwidth, nominal level, power level (e.g., in decibels), and potential level (e.g., in volts). In some cases, relationship between power and potential for an audio signal may be related to an impedance of a signal path of the audio signal. In some cases, a signal path may single-ended or balanced.

With continued reference to FIG. 1, processor 104 may be in communication with at least an eye sensor 112 and/or at least a speech sensor 116. Processor 104 may communicate with at least an eye sensor 112 and/or at least a speech sensor 116 using any method, including by way of communication signals. As used in this disclosure, a "signal" is any intelligible representation of data, for example from one device to another. A signal may include an optical signal, a hydraulic signal, a pneumatic signal, a mechanical, signal, an electric signal, a digital signal, an analog signal and the like. In some cases, a signal may be used to communicate with a computing device (processor 104), for example by way of one or more ports. In some cases, a signal may be transmitted and/or received by a computing device (processor 104) for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

Still referring to FIG. 1, in some cases, system 100, for instance at least an eye sensor 112, at least a speech sensor 120, and/or processor 104 may perform one or more signal processing steps on a signal. For instance, system 100 may analyze, modify, and/or synthesize a signal representative of data in order to improve the signal, for instance by improving transmission, storage efficiency, or signal to noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which varying continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1, processor 104 may receive one or more of at least an eye parameter 116 and at least a speech parameter 124. In some cases, processor 104 determine at least an eye pattern 128 as a function of the at least an eye parameter 116. As used in this disclosure, an "eye pattern" is a representation of an eye-related behavioral phenomenon. In some cases, an eye pattern 128 may be derived or otherwise determined from an eye parameter 116. In some cases, eye parameters 116 (e.g., images from optical tracker or electrical signals from electromyography sensor) may be used to ascertain eye movements 116. Eye movements 116 may be divided into fixations and saccades. Fixations may occur when eye gaze pauses in a certain position. Saccades may occur when eye gaze moves to another position. A resulting series of fixations and saccades may be called a scanpath 116. Smooth pursuit describes a scanpath of an eye following a moving object. Fixational eye movements 116 include microsaccades: small, involuntary saccades that occur during attempted fixation. Most information from an eye is made available to a viewer 108 during a fixation or smooth pursuit, but not during a saccade. Scanpaths 116 may be useful for analyzing cognitive intent, interest, and salience. Other biological factors may affect the scanpath 116 as well. In some cases, eye parameter may include 116 include blink rate. As used in this disclosure, is any time related variable associated with movement of an eyelid. Exemplary, blink rates include number of blinks over a certain time, average frequency of blinks, amount of time per blink, delay time between stimulation and a blink (e.g., corneal reflex), and the like.

Still referring to FIG. 1, in some embodiments, processor 104 may determine at least an eye pattern 128 using one or more machine learning processes. Exemplary machine learning processes are described in detail with reference to FIGS. 5-8. For example, in some cases, processor 104 may receive an eye pattern training data. As used in this disclosure, "eye pattern training data" is a training set that correlates eye parameters to eye patterns. In some cases, eye pattern training data may be compiled from historic information, for instance by a user. In some cases, eye pattern training data may be compiled by an unsupervised machine learning process. Eye pattern training data may use eye parameters correlated to eye patterns for one individual user, or for a cohort or population of users. Historic information may include information from eye-related study. In some cases, historical information may include information captured from use of system 100. Processor 104 may input eye pattern training data into an eye pattern machine learning algorithm. As used in this disclosure, an "eye pattern machine learning algorithm" is any machine learning algorithm that is configured to train an eye pattern machine learning model using eye pattern training data. Processor 104 may train an eye pattern machine learning model 136, as a function of eye pattern machine learning algorithm. As used in this disclosure, "eye pattern machine learning model" is a machine learning model that is configured to take as input at least an eye parameter and output at least a correlated eye pattern. Processor 104 may determine at least an eye pattern 128 as a function of eye pattern machine learning model 136 and at least an eye parameter 116.

With continued reference to FIG. 1, processor 104 may determine at least a speech pattern 132 as a function of the at least a speech parameter 124. As used in this disclosure, a "speech pattern" is a representation of a speech-related behavioral phenomenon. In some cases, a speech pattern may be derived or otherwise determined from a speech parameter. Exemplary speech patterns include timber, pitch, and cadence of speech. In some cases, speech pattern may be unrelated to content of an actor's 108 speech. Instead, in some cases, speech pattern 132 may be related to changes audible characteristics of actor's speech. In some cases, speech pattern 132 may be derived through analysis of speech parameters 124, for instance audio analysis described above. Speech pattern 132 may include one or more prosodic variables. As used in this disclosure, "prosodic variables" are variables that relate to spoken syllables or larger speech units. In some cases, speech pattern 132 may include audible variables, for instance pitch, change in pitch, length of units of speech (e.g., syllables), volume, loudness, prominence (i.e., relative volume of a unit speech, timbre, quality of sound, and the like. In some cases, speech pattern 132 may include acoustic terms. Acoustic terms may include without limitation fundamental frequency, duration, intensity, sound pressure, spectral characteristics, and the like. Speech pattern 132 may include speech tempo. As used in this disclosure, "speech tempo" is a measure of a number of speech units within a certain amount of time. Speech tempo may vary within speech of one person, for instance according to context and emotional factors. Speech tempo may have units of syllables per second.

Still referring to FIG. 1, in some embodiments, processor 104 may be configured to determine a speech pattern 132 by using one or more machine learning processes. Exemplary machine learning processes are described in detail with reference to FIGS. 5-8. For example, in some cases, processor 104 may receive a speech pattern training data. As used in this disclosure, "speech pattern training data" is a training set that correlates speech parameters to speech patterns. In some cases, speech pattern training data may be compiled from historic information, for instance by a user. In some cases, speech pattern training data may be compiled by an unsupervised machine learning process. Speech pattern training data may use speech parameters correlated to speech patterns for one individual user, or for a cohort or population of users. Historic information may include information from speech-related study. In some cases, historical information may include information captured from use of system 100. Processor 104 may input speech pattern training data into a speech pattern machine learning algorithm. As used in this disclosure, a "speech pattern machine learning algorithm" is any machine learning algorithm that is configured to train a speech pattern machine learning model using speech pattern training data. Processor 104 may train a speech pattern machine learning model 140, as a function of speech pattern machine learning algorithm. As used in this disclosure, "speech pattern machine learning model" is a machine learning model that is configured to take as input at least a speech parameter and output at least a correlated speech pattern. Processor 104 may determine at least a speech pattern 132 as a function of speech pattern machine learning model 140 and at least a speech parameter 124.

With continued reference to FIG. 1, processor 104 may correlate one or more of at least an eye pattern 128 and at least a speech pattern 132 to a cognitive status 144 As used in this disclosure, "cognitive status" is a representation of mental performance. Exemplary cognitive statuses may include classifications, for instance impaired or unimpaired. Alternatively or additionally, cognitive status may include a relative or absolute continuously variable measure that indicates performance. For example, cognitive status may be represented as a proportion or percentage relative an ideal or satisfactory cognitive performance. Cognitive performance can be pegged relative a user's performance. Alternatively or additionally, in some cases, cognitive performance may be pegged relative a level of cognitive performance required for a given task or responsibility.

Still referring to FIG. 1, in some embodiments, processor 104 may be configured to determine a cognitive status 144 by using one or more machine learning processes. In some embodiments, processor may determine cognitive status 144 from one or more behavioral parameters. Exemplary machine learning processes are described in detail with reference to FIGS. 5-8. In some cases, processor 104 may receive a cognitive status training data. As used in this disclosure, "cognitive status training data" is a training set that correlates behavioral parameters, such as without limitation eye patterns, eye parameters, speech patterns, and speech parameters to cognitive statuses. A "behavioral parameter," for the purposes of this disclosure is a characteristic of physiological phenomena. Behavioral parameters may include eye patterns eye parameters, speech patterns, speech parameters, and the like. In some embodiments, behavioral parameters may include any physiological parameters disclosed in this disclosure. Behavioral parameters may include, as non-limiting examples, hematological parameters, circulatory parameters, blood oxygen levels, blood pressures, neurological oscillations, hydration parameters, optical parameters, neural activity parameters, respiratory parameters, and the like. In some cases, cognitive status training data may be compiled and/or correlated from historic information, for instance by a user. In some cases, cognitive status training data may be compiled and/or correlated by an unsupervised machine learning process. Cognitive status training data may use behavioral parameters correlated to cognitive status for one individual user, or for a cohort or population of users. Historic information may include information from cognitive status-related study. In some cases, historical information may include information captured from use of system 100. Processor 104 may input cognitive status training data into a cognitive status machine learning algorithm. As used in this disclosure, an "cognitive status machine learning algorithm" is any machine learning algorithm that is configured to train a cognitive status machine learning model using cognitive status training data. Processor 104 may train a cognitive status machine learning model 148, as a function of the cognitive status machine learning algorithm. As used in this disclosure, "cognitive status machine learning model" is a machine learning model that is configured to take as input at least a behavioral parameter, such as without limitation eye patterns, eye parameters, speech patterns, and speech parameters, and output at least a correlated cognitive status. Processor 104 may determine cognitive status 144 as a function of cognitive status machine learning model 148 and one or more of at least an eye pattern 128 and the least a speech pattern 132.

Still referring to FIG. 1, in some cases one or more of eye machine learning model 136, speech machine learning model 140, and cognitive status machine learning model 148 may include a classifier, such as any classifier described in detail below. In some cases, classifier may include calculation of distance. For instance classifier may employ fuzzy sets having coverages based on distances from different centroids/neighbors (e.g., probability of set membership based on degree of closeness to a corresponding classification). In some cases, classifier may include a fuzzy inference engine configured to determine one or more classification set membership probability determinations. Inference engine may include a sum-product, max-product, min-max engine, or the like. In some cases, classifier may perform one or more rules and/or actions as a function of output from fuzzy inference engine, thereby dealing with different overlapping fuzzy sets (i.e., classifications). Fuzzy set classification is described in greater detail with reference to FIG. 8 below.

Still referring to FIG. 1, in some embodiments, processor 104 may be additionally configured to correlate one or more of at least an eye parameter 116 and at least a speech parameter 124 to the cognitive status 144. For instance, in some cases, processor 104 may make a determination of cognitive status 144 without an intervening step of determining a speech pattern 132 and/or an eye pattern 128.

Still referring to FIG. 1, in some embodiments, processor 104 may be additionally configured to determine a confidence metric associated with correlation and/or determination of cognitive status 144. As used in this disclosure, a "confidence metric" is a quantified expression of confidence associated with a function, such as a likelihood or probability that an output of a function is accurate or correct. Determination of a confidence metric may include any appropriate process described in this disclosure, including for example with reference to FIGS. 5-8. Exemplary processes for determining a confidence metric include, without limitation, fuzzy mathematics (see FIG. 8), as well as calculation of a distance metric (see FIG. 5). In some cases, a confidence metric may be a proportional or unitless figure, for example expressed in terms of a proportion or percentage. Alternatively of additionally, a confidence metric may be represented using relative or absolute units. In some cases, a confidence metric may be compared to a threshold confidence metric in order to determine suitability of an associated correlation and/or determination, for example of a cognitive status 144. For instance, in some cases a confidence metric no less than a threshold confidence metric of 95%, 90%, 85%, 75%, or 50% is required in order to assure an underlying correlation and/or determination of cognitive status is "correct."

Figure 2:
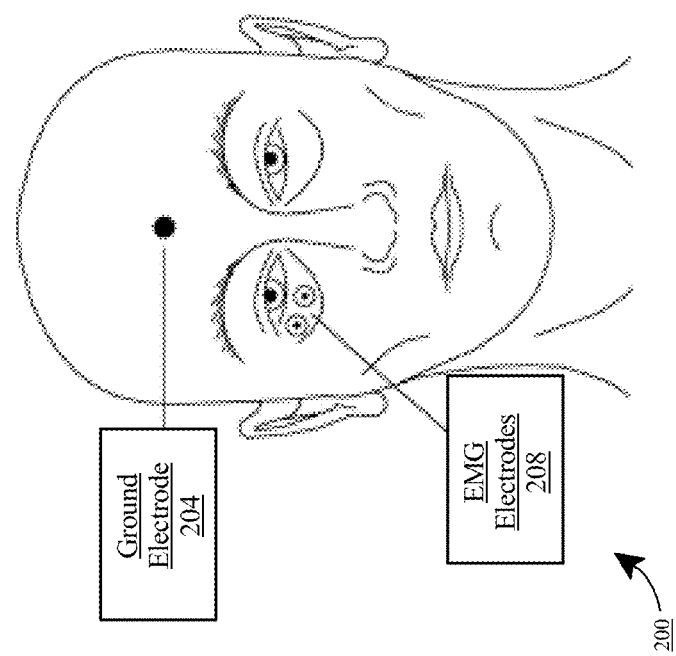
FIG. 2 illustrates an exemplary electromyography sensor.

Referring now to FIG. 2 an exemplary electromyography (EMG) sensor 200 is illustrated. In some cases, electromyography (EMG) may be an electrodiagnostic medicine technique for evaluating and recording electrical activity produced by skeletal muscles. EMG may be performed using an instrument called an electromyograph to produce a record called an electromyogram. An electromyograph may detect electric potential generated by muscle cells, for instance when these cells are electrically or neurologically activated. Resulting electromyographic signals can be analyzed to detect medical abnormalities, activation level, or recruitment order, or to analyze the biomechanics of human or animal movement. In some cases, EMG may also be used as middleware in gesture recognition towards allowing input of physical action to a computing device or as a form of human-computer interaction. In some cases, an EMG sensor 200 may be located about an eye of a user and used to detect eye movements and/or blinks, for instance through detection of electrical activity of extraocular muscles. An EMG sensor 200 may include at least a ground electrode 204 and at least an EMG electrode 208. In some cases, a ground electrode 204 may be placed substantially away from an eye and/or extraocular muscles. In some cases, a ground electrode 204 may be electrically isolated (i.e., floating), thereby allowing detection of muscular electrical activity relative the body rather than relative a ground or other reference. In some cases, EMG signals may be substantially made up of superimposed motor unit action potentials (MUAPs) from several motor units (e.g., muscles). EMG signals can be decomposed into their constituent MUAPs. MUAPs from different motor units tend to have different characteristic shapes, while MUAPs recorded by the same electrode from the same motor unit are typically similar. Notably MUAP size and shape depend on where the electrode is located with respect to muscle fibers and so can appear different if an electrode 204, 208 moves position. EMG decomposition may involve any signal processing methods described in this disclosure, including those below.

With continued reference to FIG. 2, in some case EMG signal rectification may include translation of a raw EMG signal to a signal with a single polarity, for instance positive. In some cases, rectifying an EMG signal may be performed to ensure the EMG signal does not average to zero, as commonly a raw EMG signal may have positive and negative components. According to some embodiments, substantially two types of EMG signal rectification may be used full-wave and half-wave rectification. As used in this disclosure, "full-wave rectification" may add EMG signal below a baseline to the EMG signal above the baseline, thereby resulting in a conditioned EMG signal that is all positive. For example, if baseline of EMG signal is zero, full-wave rectification would be equivalent to taking an absolute value of the EMG signal. According to some embodiments, full-wave rectification may conserve substantially all of EMG signal energy for analysis. As used in this disclosure, "half-wave rectification" discards a portion of EMG signal below baseline. As a result of half-wave rectification, average of EMG signal may no longer be zero; therefore, an EMG signal conditioned by half-wave rectification can be used in further statistical analyses. In some cases, EMG signal measurement may be performed at a rate no less than 1 Hz, 10 Hz, 100 Hz, 1 Khz, 10 KHz, or 100 KHz.

Still referring to FIG. 2, in some embodiments, EMG sensor 200 may detect eye parameters that can be analyzed, for example using processor 104, by way of time of arrival or time difference of arrival methods. As used in this disclosure, "time of arrival" is an absolute time when a signal reaches a receiver. In some cases, a plurality of EMG electrodes 308 may be located at different locations proximal an eye. Difference in time of arrival of signals between EMG electrodes 308 can be indicative of physiological phenomena. In some cases, propagation velocity may be determined. Propagation velocity may be a measure of distance over time, for instance distance a signal has traveled over time for signal to travel. In some cases, propagation velocity of EMG signals may be used to determine eye patterns. For instance, in some cases, blink rate may be ascertained from propagation velocity and/or other time of arrival metrics.

Still referring to FIG. 2, in some embodiments, EMG sensor 200 may be used to detect a gaze of user and/or the gaze of the user over time. As used in this disclosure, "gaze" is a direction a user is looking. As used in this disclosure "gaze vector" is a directional vector having a point located at a user's eye (e.g., pupil, retina, or the like) which represents a gaze of the user. In some cases, an EMG sensor 200 may be used to detect a gaze of a user over time and this information may be used as input for one or more machine-learning models described herein. In some cases, eye parameters from EMG sensor 200 may be used as input for an eye pattern machine learning process that used to determine an eye pattern (e.g., gaze vector, scan path, blink rate, or the like). Alternatively or additionally, in some cases, eye parameters and/or eye patterns, such as a user's blink rate as detected by EMG sensor 200, may be used as an input for a cognitive status machine learning process. This is because, for example, users who blink more frequently may be less attentive (e.g., drowsier) than those who blink less. For example, in an extreme case a user whose eyes are closed for prolonged periods of time may be found to be inattentive, perhaps even asleep.

In an embodiment, systems, devices and methods disclosed herein detect physiological parameters such as blood oxygen level, blood pressure, neurological oscillations, and heart rate of a user who is operating an item of equipment such as an aircraft through nonintrusive means. Sensors mounted in optimal locations on the head or neck of the user may detect physiological parameters accurately, minimizing interference in activities the user engages in while obtaining a clearer signal than otherwise would be possible. Embodiments of the disclosed device may provide users such as pilots, firemen, and divers who are operating under extreme circumstances with an early warning regarding potential crises such as loss of consciousness, affording the user a few precious extra seconds to avert disaster. Alarms may be provided to the user via bone-conducting transducers or by integration into displays the user is operating, increasing the likelihood that the user will notice the warning in time. Embodiments of devices, systems, and methods herein may enable training for pilots or other persons to function within physiological limitations imposed by their environment, such as hypoxemia imposed by altitude, high G forces and the like; training may further enable users to learn how to avoid total impairment, and to function under partial impairment.

Figure 3A:
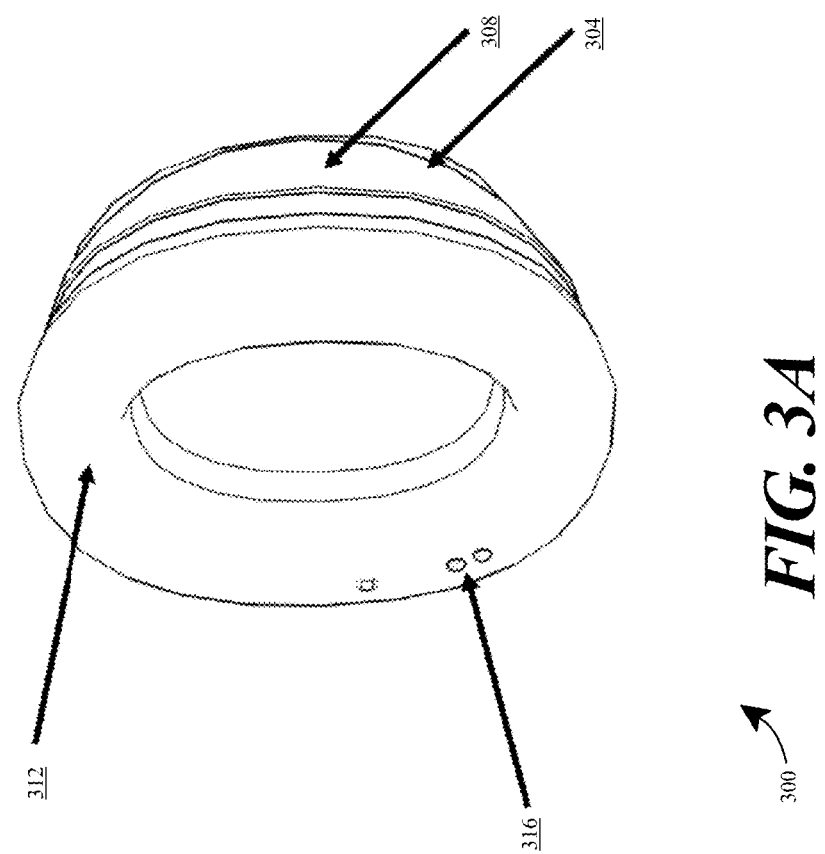
FIG. 3A shows a perspective view of a device according to an embodiment disclosed herein.
Figure 3B:
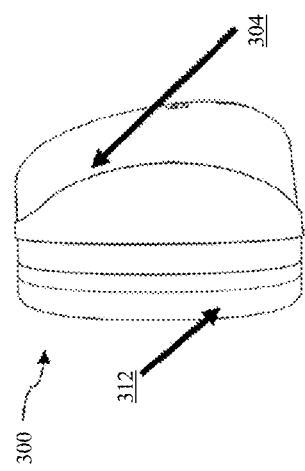
FIG. 3B shows a front view of a device according to an embodiment disclosed herein.
Figure 3C:
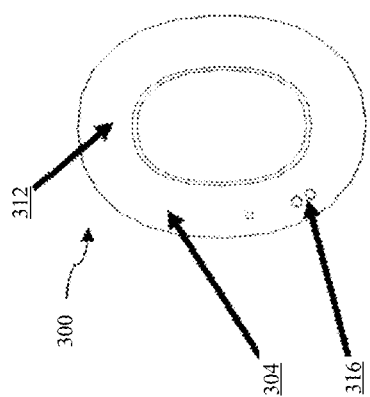
FIG. 3C shows a side view of a device according to an embodiment disclosed herein.
Figure 3D:
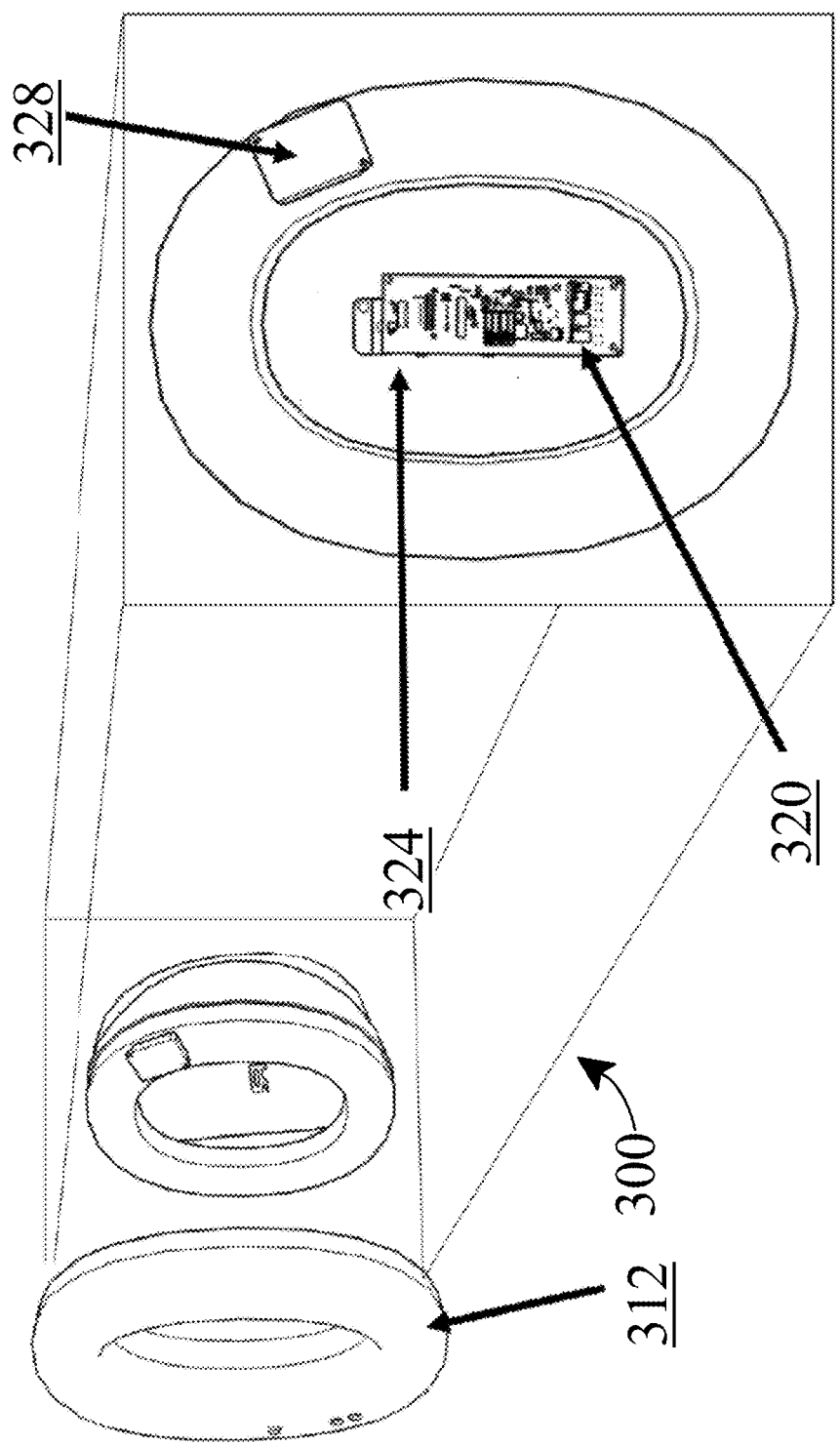
FIG. 3D shows a perspective view of a device according to an embodiment disclosed herein.
Figure 3E:
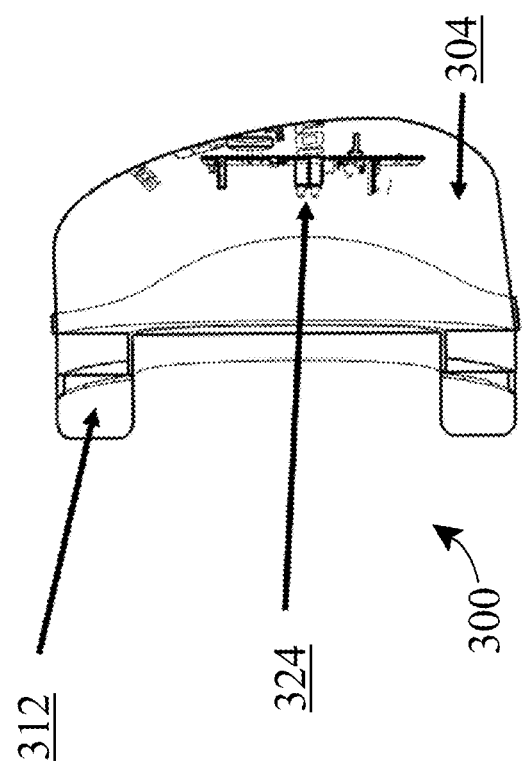
FIG. 3E shows a front sectional view of a device according to an embodiment disclosed herein.

Referring now to FIGS. 3A-3E, an exemplary embodiment of a perspective view (FIG. 3A), a side view (FIG. 3B), a front view (FIG. 3C), a perspective view (FIG. 3D), and a front sectional view (FIG. 3E) of a device for measuring physiological parameters 300 is illustrated. Referring now to FIG. 3A, device for measuring physiological parameters 300 includes a housing 304. Housing 304 may be mounted to an exterior body surface of a user; exterior body surface may include, without limitation, skin, nails such as fingernails or toenails, hair, an interior surface of an orifice such as the mouth, nose, or ears, or the like. A locus on exterior body surface for mounting of housing 304 and/or other components of device may be selected for particular purposes as described in further detail below. Exterior body surface and/or locus may include an exterior body surface of user's head, face, or neck. Housing 304 may be constructed of any material or combination of materials, including without limitation metals, polymer materials such as plastics, wood, fiberglass, carbon fiber, or the like. Housing 304 may include an outer shell 308. Outer shell 308 may, for instance, protect elements of device 300 from damage, and maintain them in a correct position on a user's body as described in further detail below. Housing 304 and/or outer shell 308 may be shaped, formed, or configured to be inserted between a helmet worn on a head of the user and the exterior body surface; housing 304 and/or outer shell 308 may be shaped to fit between the helmet and the exterior body surface. As a non-limiting example, exterior body surface may be a surface, such as a surface of the head, face, or neck of user, which is wholly or partially covered by helmet, as described for example in further detail below. As a further non-limiting example, housing 304 may be formed to have a similar or identical shape to a standard-issue "ear cup" incorporated in an aviation helmet, so that housing 304 can replace ear cup after ear cup has been removed; in an embodiment, device 300 may incorporate one or more elements of ear-cup, including sound-dampening properties, one or more speakers or other elements typically used to emit audio signals in headsets or headphones, or the like. As a non-limiting example, device 300, housing 304, and/or shell may form a form-fit replacement for standard earcups found in military flight helmets. Shell may be rigid, where "rigid" is understood as having properties of an exterior casing typically used in an earcup, over-ear headphone, hearing protection ear covering, or the like; materials used for such a shell may include, without limitation, rigid plastics such as polycarbonate shell plastics typically used in helmets and hardhats, metals such as steel, and the like. Persons skilled in the art, upon reading the entirety of this disclosure, will understand "rigid" in this context as signifying sufficient resistance to shear forces, deformations, and impacts to protect electronic components as generally required for devices of this nature.

Still viewing FIGS. 3A-3E, housing 304 may include a seal 312 that rests against exterior body surface when housing 304 is mounted thereon. Seal 312 may be pliable; seal 312 may be constructed of elastomeric, elastic, or flexible materials including without limitation flexible, elastomeric, or elastic rubber, plastic, silicone including medical grade silicone, gel, and the like. Pliable seal 312 may include any combination of materials demonstrating flexible, elastomeric, or elastic properties, including without limitation foams covered with flexible membranes or sheets of polymer, leather, or textile material. As a non-limiting example, pliable seal 312 may include any suitable pliable material for a skin-contacting seal portion of an earcup or other device configured for placement over a user's ear, including without limitation any pliable material or combination of materials suitable for use on headphones, headsets, earbuds, or the like. In an embodiment, pliable seal 312 advantageously aids in maintaining housing 304 and/or other components of device 300 against exterior body surface; for instance, where exterior body surface has elastomeric properties and may be expected to flex, stretch, or otherwise alter its shape or position to during operation, pliable seal 312 may also stretch, flex, or otherwise alter its shape similarly under similar conditions, which may have the effect of maintaining seal 312 and/or one or more components of device 300 as described in greater detail below, in consistent contact with the exterior body surface. Seal 312 may be attached to housing 304 by any suitable means, including without limitation adhesion, fastening by stitching, stapling, or other penetrative means, snapping together or otherwise engaging interlocking parts, or the like. Seal 312 may be removably attached to housing 304, where removable attachment signifies attachment according to a process that permits repeated attachment and detachment without noticeable damage to housing 304 and/or seal 312, and without noticeable impairment of an ability to reattach again by the same process. As a non-limiting example, pliable seal 312 may be placed on an ear cup (for instance shown for exemplary purposes in FIG. 3) of the housing 304; pliable seal may be formed of materials and/or in a shape suitable for use as an ear seal in an ear cup of a helmet, an over-ear headphone or hearing protection device, or the like. Persons skilled in the art, upon reviewing this disclosure in its entirety, will be aware of forms and material properties suitable for use as seal 312, including without limitation a degree and/or standard of pliability required and/or useful to function as a seal 312 in this context.

With continued reference to FIGS. 3A-3E, housing 304 may include, be incorporated in, or be attached to an element containing additional components to device 300. For instance, in an embodiment, housing 304 may include, be incorporated in, or be attached to a headset; headset may include, without limitation, an aviation headset, such as headsets as manufactured by the David Clark company of Worcester Massachusetts, or similar apparatuses. In some embodiments, housing 104 is headset; that is, device 300 may be manufactured by incorporating one or more components into the headset, using the headset as a housing 304. As a further non-limiting example, housing 304 may include a mask; a mask as used herein may include any device or element of clothing that is worn on a face of user during operation, occluding at least a part of the face. Masks may include, without limitation, safety googles, gas masks, dust masks, self-contained breathing apparatuses (SCBA), self-contained underwater breathing apparatuses (SCUBA), and/or other devices worn on and at least partially occluding the face for safety, functional, or aesthetic purposes. Housing 304 may be mask; that is, device 300 may be manufactured by incorporating one or more elements or components of device 300 in or on mask, using mask as housing 304. Housing 304 may include, be incorporated in, or be attached to an element of headgear, defined as any element worn on and partially occluding a head or cranium of user. Headgear may wholly or partially occlude user's face and thus also include a mask; headgear may include, for instance, a fully enclosed diving helmet, space helmet or helmet incorporated in a space suit, or the like. Headgear may include a headband, such as without limitation a headband of a headset, which may be an aviation headset. Headgear may include a hat. Headgear may include a helmet, including a motorcycle helmet, a helmet used in automobile racing, any helmet used in any military process or operation, a construction "hardhat," a bicycle helmet, or the like. In an embodiment, housing 304 is shaped to conform to a particular portion of user anatomy when placed on exterior body surface; when placed to so conform, housing 304 may position at least a sensor and/or user-signaling device 328 in a locus chosen as described in further detail below. For instance, where housing 304 is incorporated in a helmet, mask, earcup or headset, housing 304 may be positioned at a particular portion of user's head when helmet, mask, earcup or headset is worn, which may in turn position at least a sensor and/or user-signaling device 328 at a particular locus on user's head or neck.

Continuing to refer to FIGS. 3A-3E, device 300 includes at least a physiological sensor 316. At least a physiological sensor 316 is configured to detect at least a physiological parameter and transmit an electrical signal as a result of the detection; transmission of an electrical signal, as used herein, includes any detectable alternation of an electrical parameter of an electrical circuit incorporating at least a physiological sensor 316. For instance, at least a physiological sensor 316 may increase or reduce the impedance and/or resistance of a circuit to which at least a physiological sensor 316 is connected. At least a physiological sensor 316 may alter a voltage or current level, frequency, waveform, amplitude, or other characteristic at a locus in circuit. Transmission of an electrical signal may include modulation or alteration of power circulating in circuit; for instance transmission may include closing a circuit, transmitting a voltage pulse through circuit, or the like. Transmission may include driving a non-electric signaling apparatus such as a device for transmitting a signal using magnetic or electric fields, electromagnetic radiation, optical or infrared signals, or the like.

Still referring to FIGS. 3A-3E, at least a physiological parameter may include any datum that may be captured by a sensor and describing a physiological state of user. At least a physiological parameter may include at least a circulatory and/or hematological parameter, which may include any detectable parameter describing the state of blood vessels such as arteries, veins, or capillaries, any datum describing the rate, volume, pressure, pulse rate, or other state of flow of blood or other fluid through such blood vessels, chemical state of such blood or other fluid, or any other parameter relative to health or current physiological state of user as it pertains to the cardiovascular system. As a non-limiting example, at least a circulatory parameter may include a blood oxygenation level of user's blood. At least a circulatory parameter may include a pulse rate. At least a circulatory parameter may include a blood pressure level. At least a circulatory parameter may include heart rate variability and rhythm. At least a circulatory parameter may include a plethysmograph describing user blood-flow; in an embodiment, plethysmograph may describe a reflectance of red or near-infrared light from blood. One circulatory parameter may be used to determine, detect, or generate another circulatory parameter; for instance, a plethysmograph may be used to determine pulse and/or blood oxygen level (for instance by detecting plethysmograph amplitude), pulse rate (for instance by detecting plethysmograph frequency), heart rate variability and rhythm (for instance by tracking pulse rate and other factors over time), and blood pressure, among other things. At least a physiological sensor may be configured to detect at least a hematological parameter of at least a branch of a carotid artery; at least a physiological parameter may be positioned to capture the at least a hematological parameter by placement on a location of housing that causes at least a physiological sensor to be placed in close proximity to the at least a branch; for instance, where housing is configured to be mounted to a certain location on a user's cranium, and in a certain orientation, such as when housing forms all or part of a helmet, headset, mask, element of headgear, or the like, at least a physiological sensor may include a sensor so positioned on the housing or an extension thereof that it will contact or be proximate to a locus on the user's skin under which the at least a branch runs. As a non-limiting example, where device 300 forms an earcup or earphone, at least a physiological sensor 316 may include a sensor disposed on or embedded in a portion of the earcup and/or earphone contacting a user's skin over a major branch of the external carotid artery that runs near or past the user's ear.

In an embodiment, and still viewing FIGS. 3A-3E, detection of hematological parameters of at least a branch of a carotid artery may enable device 300 to determine hematological parameters of a user's central nervous system with greater accuracy than is typically found in devices configured to measure hematological parameters. For instance, a blood oxygen sensor placed on a finger or other extremity may detect low blood oxygen levels in situations in which the central nervous system is still receiving adequate oxygen, because a body's parasympathetic response to decreasing oxygen levels may include processes whereby blood perfusion to the appendages is constricted in order to sustain higher oxygen levels to the brain; in contrast, by directly monitoring the oxygenation of a major branch of the external carotid artery, the measurement of oxygenation to the central nervous system may be more likely to achieve a more accurate indication of oxygen saturation than a peripheral monitor. Use of the carotid artery in this way may further result in a more rapid detection of a genuine onset of hypoxemia; as a result, a person such as a pilot that is using device 300 may be able to function longer under conditions tending to induce hypoxemia, knowing that an accurate detection of symptoms may be performed rapidly and accurately enough to warn the user. This advantage may both aid in and be augmented by use with training processes as set forth in further detail below.

With continued reference to FIGS. 3A-3E, at least a physiological sensor 316 may include a hydration sensor; hydration sensor may determine a degree to which a user has an adequate amount of hydration, where hydration is defined as the amount of water and/or concentration of water versus solutes such as electrolytes in water, in a person's body. Hydration sensor may use one or more elements of physiological data, such as sweat content and/or hematological parameters detected without limitation using plethysmography, to determine a degree of hydration of a user; degree of hydration may be associated with an ability to perform under various circumstances. For instance, a person with adequate hydration may be better able to resist the effects of hypoxemia in high-altitude and/or high-G for longer or under more severe circumstances, either because the person's body is better able to respond to causes of hypoxemia and delay onset, or because the person is better able to cope with diminished blood oxygen; this may be true of other conditions and/or physiological states detected using at least a physiological sensor 316, and may be detected using heuristics or relationships derived, without limitation, using machine learning and/or data analysis as set forth in further detail below.

Still referring to FIGS. 3A-3E, at least a physiological sensor 316 may include a volatile organic compound (VOC) sensor. VOC sensor may sense VOCs, including ketones such as acetone; a user may emit ketones in greater quantities when undergoing some forms of physiological stress, including without limitation hypoglycemia resulting from fasting or overwork, which sometimes results in a metabolic condition known as ketosis. As a result, detections of higher quantities of ketones may indicate a high degree of exhaustion or low degree of available energy; this may be associated with a lessened ability to cope with other physiological conditions and/or parameters that may be detected by or using at least a physiological sensor 316, such as hypoxemia, and/or environmental stressors such as high altitude or G-forces. Such associations may be detected or derived using data analysis and/or machine learning as described in further detail below.

With continued reference to FIGS. 3A-3E, at least a physiological parameter may include neural oscillations generated by user neurons, including without limitation neural oscillations detected in the user's cranial region, sometimes referred to as "brainwaves." Neural oscillations include electrical or magnetic oscillations generated by neurological activity, generally of a plurality of neurons, including superficial cranial neurons, thalamic pacemaker cells, or the like. Neural oscillations may include alpha waves or Berger's waves, characterized by frequencies on the order of 7.5-12.5 Hertz, beta waves, characterized by frequencies on the order of 13-30 Hertz, delta waves, having frequencies ranging from 1-4 Hertz, theta waves, having frequencies ranging from 4-8 Hertz, low gamma waves having frequencies from 30-70 Hertz, and high gamma waves, which have frequencies from 70-150 Hertz. Neurological oscillations may be associated with degrees of wakefulness, consciousness, or other neurological states of user, for instance as described in further detail below. At least a sensor may detect body temperature of at least a portion of user's body, using any suitable method or component for temperature sensing.

Figure 6:
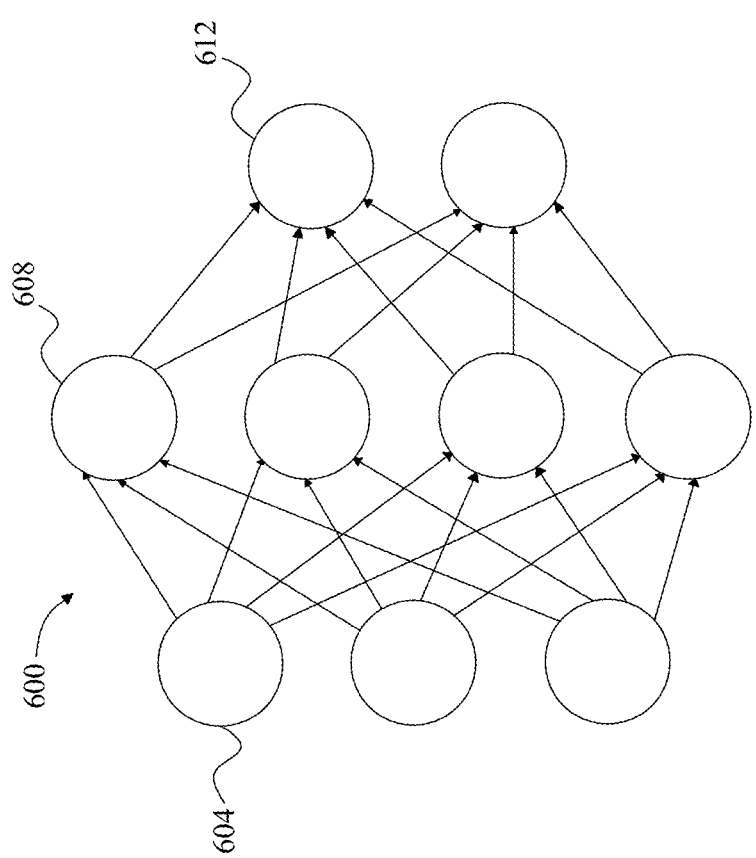
FIG. 6 is a block diagram illustrating an exemplary nodal network.

Still referring to FIGS. 3A-3E, at least a physiological sensor 316 may include an optical sensor, which detects light emitted, reflected, or passing through human tissue. Optical sensor may include a near-infrared spectroscopy sensor (NIRS). A NIRS, as used herein, is a sensor that detects signals in the near-infrared electromagnetic spectrum region, having wavelengths between 780 nanometers and 2,500 nanometers. FIG. 6 illustrates an exemplary embodiment of a NIRS 600 against an exterior body surface, which may include skin. NIRS 600 may include a light source 604, which may include one or more light-emitting diodes (LEDs) or similar element. Light source 604 may, as a non-limiting example, convert electric energy into near-infrared electromagnetic signals. Light source 604 may include one or more lasers. NIRS 600 may include one or more detectors 608 configured to detect light in the near-infrared spectrum. Although the wavelengths described herein are infrared and near-infrared, light source 604 may alternatively or additionally emit light in one or more other wavelengths, including without limitation blue, green, ultraviolet, or other light, which may be used to sense additional physiological parameters. In an embodiment, light source may include one or more multi-wavelength light emitters, such as one or more multi-wavelength LEDs, permitting detection of blood-gas toxicology. Additional gases or other blood parameters so detected may include, without limitation $CO_2$ saturation levels, state of hemoglobin as opposed to blood oxygen saturation generally. One or more detectors 608 may include, without limitation, charge-coupled devices (CCDs) biased for photon detection, indium gallium arsenide (InGaAs) photodetectors, lead sulfide (PbS) photodetectors, or the like. NIRS 600 may further include one or more intermediary optical elements (not shown), which may include dispersive elements such as prisms or diffraction gratings, or the like. In an embodiment, NIRS 600 may be used to detect one or more circulatory parameters, which may include any detectable parameter further comprises at least a circulatory parameter. At least a physiological sensor 316 may include at least two sensors mounted on opposite sides of user's cranium.

Referring again to FIGS. 3A-3E, at least a physiological sensor 316 may include a neural activity sensor. A neural activity sensor, as used herein, includes any sensor disposed to detect electrical or magnetic phenomena generated by neurons, including cranial neurons such as those located in the brain or brainstem. Neural activity sensor may include an electroencephalographic sensor. Neural activity sensor may include a magnetoencephalographic sensor. In an embodiment, neural activity sensor may be configured to detect neural oscillations. At least a sensor may include an eye-tracking sensor, such as one or more cameras for tracking the eyes of user. Eye-tracking sensor may include, as a non-limiting example, one or more electromyographic (EMG) sensors, which may detect electrical activity of eye muscles; electrical activity may indicate activation of one or more eye muscles to move the eye and used by a circuit such as an alert circuit as described below to determine a movement of user's eyeball, and thus its current location of focus.

Continuing to refer to FIGS. 3A-3E, device 300 may communicate with one or more physiological sensors that are not a part of device 300; one or more physiological sensors may include any sensor suitable for use as at least a physiological sensor 316 and/or any other physiological sensor. Communication with physiological sensors that are not part of device may be accomplished by any means for wired or wireless communication between devices and/or components as described herein. Device may detect and/or measure at least a physiological parameter using any suitable combination of at least a physiological sensor and/or physiological sensors that are not a part of device 300. Device 300 may combine two or more physiological parameters to detect a physiological condition and/or physiological alarm condition. For instance, and without limitation, where device 300 is configured to detect hypoxic incapacitation and/or one or more degrees of hypoxemia as described in further detail below, device 300 may perform such determination using a combination of heart rate and blood oxygen saturation, as detected by one or more sensor as described above.

Still viewing FIGS. 3A-3E, at least a physiological sensor 316 may be attached to housing 304; attachment to housing 304 may include mounting on an exterior surface of housing 304, incorporation within housing 304, electrical connection to another element within housing 304, or the like. Alternatively or additionally, at least a physiological sensor 316 may include a sensor that is not attached to housing 304 or is indirectly attached via wiring, wireless connections, or the like. As a non-limiting example, at least a physiological sensor 316 and/or one or more components thereof may be coupled to the pliable seal 312. In an embodiment, at least a physiological sensor 316 may be contacting exterior body surface; this may include direct contact with the exterior body surface, or indirect contact for instance through a portion of seal 312 or other components of device 300. In an embodiment, at least a physiological sensor 316 may contact a locus on the exterior body surface where substantially no muscle is located between the exterior body surface and an underlying bone structure, meaning muscle is not located between the exterior body surface and an underlying bone structure and/or any muscle tissue located there is unnoticeable to a user as a muscle and/or incapable of appreciably flexing or changing its width in response to neural signals; such a locus may include, as a non-limiting example, locations on the upper cranium, forehead, nose, behind the ear, at the end of an elbow, on a kneecap, at the coccyx, or the like. Location at a locus where muscle is not located between exterior body surface and underlying bone structure may decrease reading interference and/or inaccuracies created by movement and flexing of muscular tissue. At least a physiological sensor 316 may contact a locus having little or no hair on top of skin. At least a physiological sensor 316 may contact a locus near to a blood vessel, such as a locus where a large artery such as the carotid artery or a branch thereof, or a large vein such as the jugular vein, runs near to skin or bone at the location; in an embodiment, such a position may permit at least a physiological sensor 316 to detect circulatory parameters as described above.

Still viewing FIGS. 3A-3E, processor 320 may incorporate or be in communication with at least a user-signaling device 328. In an embodiment, at least a user-signaling device 328 may be incorporated in device 300; for instance, at least a user-signaling device 328 may be attached to or incorporated in housing 304. Where at least a user-signaling device 328 contacts an exterior body surface of user, housing 304 may act to place at least a user-signaling device 328 in contact exterior body surface of user. Alternatively or additionally, device 300 may communicate with a user-signaling device 328 that is not incorporated in device 300, such as a display, headset, or other device provided by a third party or the like, which may be in communication with processor 320. User-signaling device 328 may be or incorporate a device for communication with an additional user-signaling device such as a vehicle display and/or helmet avionics; for instance, user-signaling device 328 may include a wireless transmitter or transponder in communication with such additional devices. In an embodiment, and without limitation, user-signaling device 328 may be configured to indicate a cognitive status to at least a user, as described in further detail below.

Continuing to refer to FIGS. 3A-3E, at least a user-signaling device 328 may include any device capable of transmitting an audible, tactile or visual signal to a user when triggered to do so by processor 320. In an embodiment, and as a non-limiting example, at least a user-signaling device 328 may include a bone-conducting transducer in vibrational contact with a bone beneath the exterior body surface. A "bone-conducting transducer," as used herein, is a device or component that bi-directionally converts an electric signal to a vibrational signal of a bone of a user." In some cases, bone of user may conduct vibrational signal to an inner-ear of user, which interprets the vibration as an audible signal. Alternatively or additionally, a bone-conducting transducer 328 may be used detect vibrational signals emanating from a user, for example during a user's speech. Bone-conducting transducer may include, for instance, a piezoelectric element, which may be similar to the piezoelectric element found in speakers or microphones, which converts an electric signal into vibrations and/or vice versa. In an embodiment, bone-conducting transducer 128 may be mounted to housing 304 in a position placing it in contact with a user's bone; for instance, where housing 304 includes or is incorporated in an ear cup, housing 304 may place bone-conducting transducer in contact with user's skull just behind the ear, over the sternocleidomastoid muscle. Likewise, where housing 304 includes a headset, mask, or helmet, housing 304 may place bone-conducting transducer in contact with a portion of user's skull that is adjacent to or covered by headset, mask, or helmet.

Still referring to FIGS. 3A-3E, at least a user-signaling device 328 may further include an audio output device. Audio output device may include any device that converts an electrical signal into an audible signal, including without limitation speakers, headsets, headphones, or the like. As a non-limiting example, audio output device may include a headset speaker of a headset incorporating or connected to device 300, a speaker in a vehicle user is traveling in, or the like. At least a user-signaling device 328 may include a light output device, which may be any device that converts an electrical signal into visible light; light output device may include one or more light source 604s such as LEDs, as well as a display, which may be any display as described below in reference to FIG. 10. At least a user-signaling device 328 may include a vehicular display; at least a vehicular display may be any display or combination of displays presenting information to a user of a vehicle user is operating. For instance, at least a vehicular display may include any combination of audio output devices, light output devices, display screens, and the like in an aircraft flight console, a car dashboard, a boat dashboard or console, or the like; processor 320 may be in communication with vehicular display using any form of communicative coupling described above, including without limitation wired or wireless connection. At least a user-signaling device 328 may include a helmet display; helmet display may include any visual, audio, or tactile display incorporated in any kind of helmet or headgear, which may be in communication with processor 320 according to any form of communicative coupling as described above.

Still viewing FIGS. 3A-3E, user-signaling device 328 and/or processor 320 may be programmed to produce a variety of indications, which may correspond to various physiological alarm conditions and/or contexts. Possible indications may be, but are not limited to imminent unconsciousness, substandard oxygenation, erratic pulse, optimum oxygenation, and/or any other suitable indication, while maintaining the spirit of the present invention. Each such indication may have a distinct pattern of audible, visual, and/or textual indications; each indication may include, for instance, an audible or textual warning or description of a physiological alarm condition. Any of the above user-signaling devices 328 and/or signals may be used singly or in combination; for instance, a signal to user may include an audio signal produced using a bone-conducting transducer, a verbal warning message output by an audio output device, and a visual display of an image or text indicating the physiological alarm condition. Persons skilled in the art, upon reviewing the entirety of this disclosure, will be aware of various combinations of signaling means and/or processes that may be employed to convey a signal to user. In an embodiment, in addition to transmitting an alarm to user-signaling device 328, alert circuit may transmit a signal to one or more automated vehicular controls or other systems to alleviate one or more environmental parameters contributing to physiological alarm condition. For instance, and without limitation, an automated aircraft control may receive an indication of hypoxia while a motion sensor indicates high acceleration; aircraft control may reduce acceleration to alleviate the hypoxia. Persons skilled in the art, upon reviewing the entirety of this disclosure, may be aware of various additional ways in which automated systems may act to alleviate a physiological alarm condition as described herein.

Figure 4:
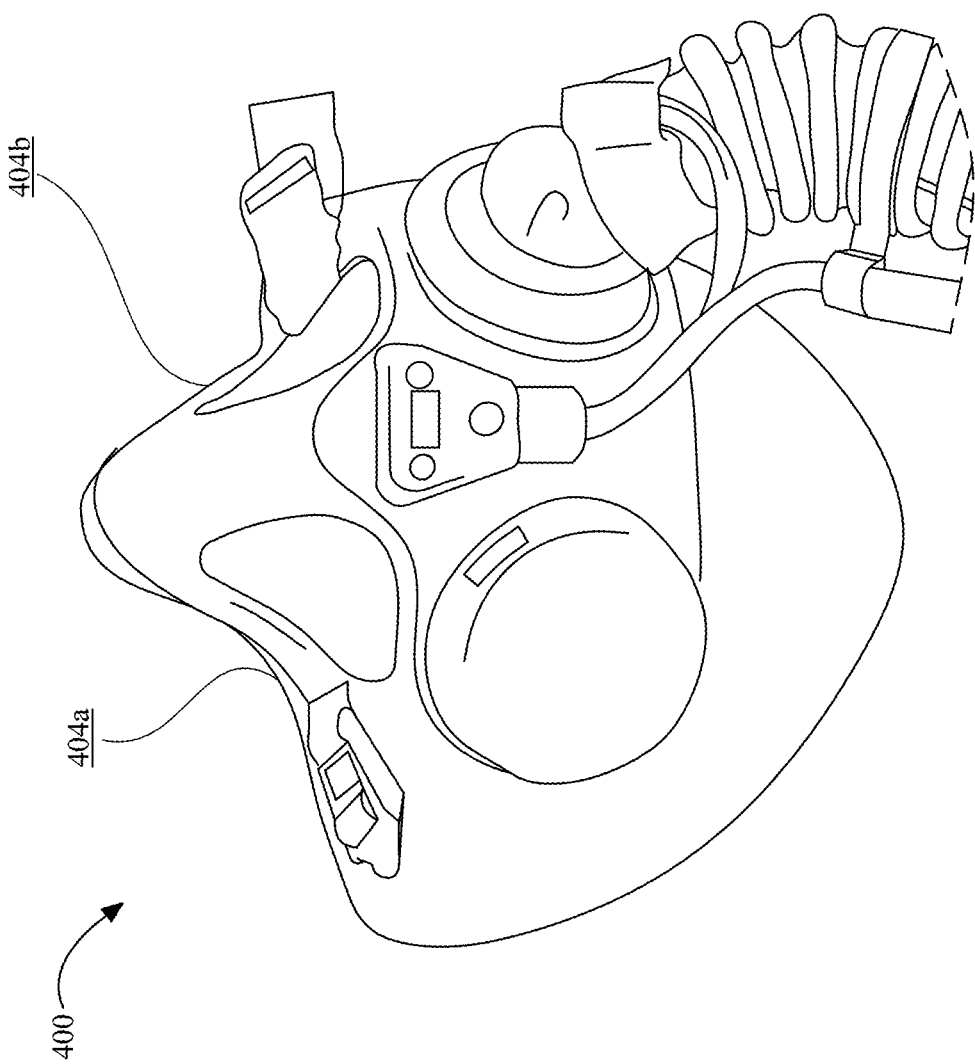
FIG. 4 illustrates an exemplary facemask.

In an embodiment, and referring now to FIG. 4, system 100 may include or otherwise be incorporated upon a mobile respiratory device 400. A "mobile respiratory device," as used herein, is a device worn on or about a face of a person, which aids in respiration, for instance when the person is in an environment where oxygen may be scarce or where other gases or particular matter such as carbon dioxide, carbon dioxide, toxic gases, droplets or fumes, or other elements that may interfere with respiration, and/or gases having ambient temperatures capable of harming a person when inhaled. Such an environment may include, without limitation, a cockpit of an aircraft such as a military aircraft, an artificially or naturally formed tunnel with an atmosphere that makes breathing difficult, such as an anoxic atmosphere, an atmosphere containing poisonous or otherwise problematic gases such as sulfur dioxide, carbon dioxide, carbon monoxide, or the like, a location at a high altitude such as a mountaintop, a location of a chemical spill and/or the like.

Still referring to FIG. 4, mobile respiratory device 400 may include, without limitation, a gas mask such as a cannister mask, a self-contained breathing apparatuses (SCBA) such as those used by firefighters, self-contained underwater breathing apparatuses (SCUBA), supplied-air respirators (SAR), particulate respirators, chemical cartridge respirators, powered air-purifying respirators (PAPRs), respirators included as part of a protective suit, airline respirators, N-95 or other NIOSH approved respirators, and/or other devices worn on and/or over and at least partially occluding the face to aid in respiration.

With continued reference to FIG. 4, an "exhaust port," as used in this disclosure, is an outlet that permits air exhaled by a user to escape from a mobile respiratory device 400. Exhaust port may include a valve such as a check-valve or other one-way valve to prevent air from entering a mobile respiratory device 400 from environment. Exhaust port may include, for instance, an exhale valve of a respirator mask or other such design. Exhaust port may also be an inlet port; for instance, air may be filtered while breathing in through the port and then exhaled, with or without filtering, via a valve at the same port.

With continued reference to FIG. 4, in some cases, mobile respiratory device 400 may include or house at least a sensor 404a-b. At least a sensor 404a-b may include any sensor described in this disclosure, including for instance EMG sensors/electrodes described in reference to FIG. 2. In some cases, mobile respiratory device 400 may allow for placement of at least an EMG electrode 404a-b proximal an eye of a user. In some cases, fewer than all EMG electrodes of a system 100 may be housed within a mobile respiratory device 400. In some cases, for instance, some EMG electrodes may be located within a mobile respiratory device 400 and some may be located within an earcup, as shown in FIGS. 3A-3E. Placement of EMG electrodes 404a-b at different locations about eye may allow for more meaningful signals to be generated, for example for time difference of arrival analysis.

Figure 5:
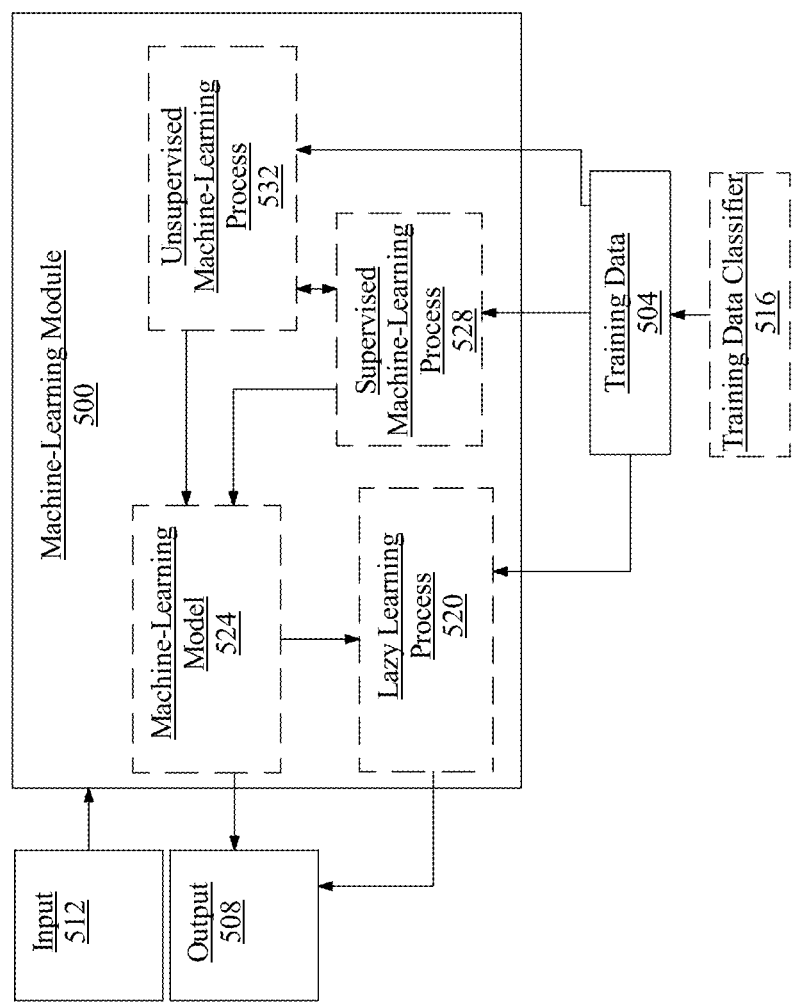
FIG. 5 is a block diagram illustrating exemplary machine learning processes.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example one or more eye patterns and speech patterns may be used as inputs and a cognitive status may be used as a correlated output.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to context. For instance, in some cases, eye and or speech parameters or patterns are likely to change dependent upon context. An emergent situation is likely to increase speech tempo, for instance. In some cases, training data may be classified according to context or circumstance. For instance, in some cases, training data may be representative of parameters or patterns related to behavioral phenomena in a resting state; alternatively training data may be classified as relating to an emergent or active state. In some cases, training data may be user or cohort specific. For example, in some cases, determination of cognitive status from sensed behavioral phenomenon may be based upon a relative change in behavior of a user (i.e., user is not acting like-herself).

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include eye patterns and/or speech patterns as described above as inputs, cognitive statuses as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Referring now to FIG. 6 an exemplary embodiment of neural network 600 is illustrated. Neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created via the process of "training" the network, in which elements from a training dataset are applied to input nodes 604, a suitable training algorithm (such as Levenberg-Marquardt, conjugate gradient, simulated annealing, or other algorithms) is then used to adjust the connections and weights between nodes in adjacent layers 608 of the neural network to produce the desired values at output nodes 612. This process is sometimes referred to as deep learning.

Figure 7:
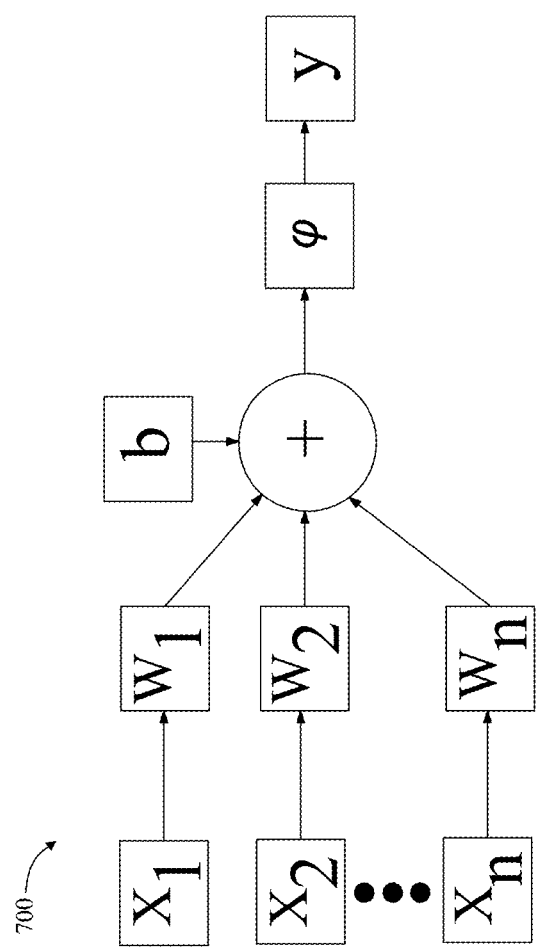
FIG. 7 is a block diagram illustrating an exemplary node.

Referring now to FIG. 7, an exemplary embodiment of a node 700 of a neural network is illustrated. A node 700 may include, without limitation a plurality of inputs $x_i$ that may receive numerical values from inputs to a neural network containing the node and/or from other nodes. Node 1000 may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 7, a neural network may receive one or more of at least an environmental parameter, at least a circulation parameter, and/or at least a respiration parameter as inputs and output one or more of a condition and/or an imminent loss of consciousness event. Alternatively or additionally in some cases, a neural network may receive one or more of at least an environmental parameter, at least a circulation parameter, and/or at least a respiration parameter as inputs and output a confidence metric representing a probability of classification to a predetermined class, for instance condition and/or imminent loss of consciousness event, according to weights $w_i$ that are derived using machine-learning processes as described in this disclosure.

Referring again to FIG. 1, In some embodiments, processor 104 may be configured to modify a training set in response to an individual user or another context. For example, processor 104 may, in some cases, retrain a machine-learning model using one or more of speech pattern and/or eye pattern correlated to cognitive status. In some embodiments, processor 104 may be configured to classify a cognitive status and determine a confidence metric. For example, in some exemplary embodiments confidence metric may be a floating-point number within a prescribed range, such as without limitation 0 to 1, with each end of the prescribed range representing an extreme representation, such as without limitation substantially no confidence and substantially absolute confidence, respectively. In some cases, confidence output may represent a relationship between a result of filtering and/or classifying. Confidence metric may be determined by one more comparisons algorithms, such as without limitation a fuzzy set comparison. For example, in some exemplary embodiments a fuzzy set comparison may be employed to compare a pattern or parameter with a membership function derived to represent at least a threshold used for classification, for instance of a cognitive status.

Figure 8:
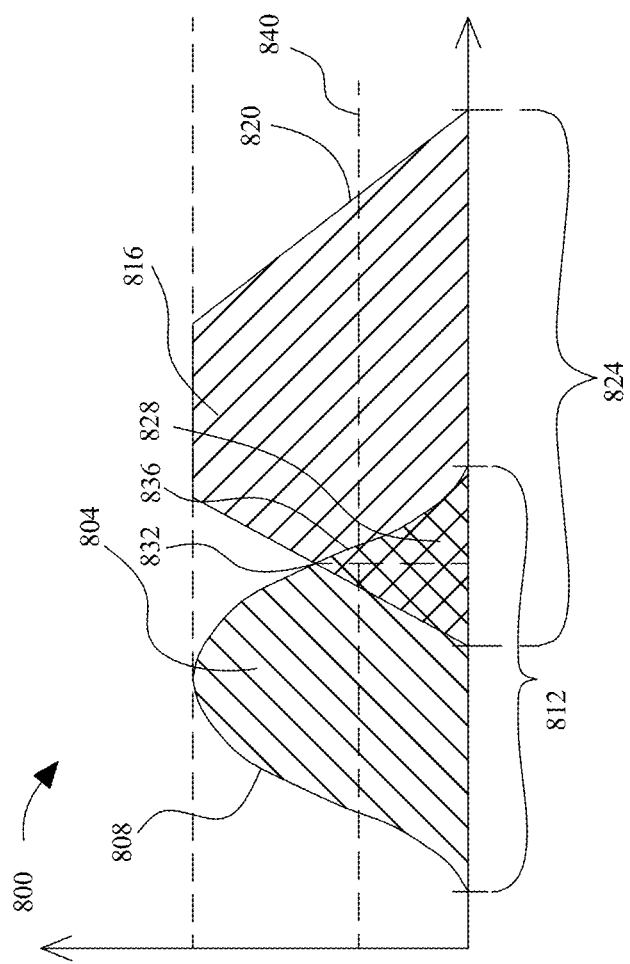
FIG. 8 is a graph illustrating exemplary fuzzy set mathematics.

Referring to FIG. 8, an exemplary embodiment of fuzzy set comparison 800 is illustrated. A first fuzzy set 804 may be represented, without limitation, according to a first membership function 808 representing a probability that an input falling on a first range of values 812 is a member of the first fuzzy set 804, where the first membership function 808 has values on a range of probabilities such as without limitation the interval [0,1], and an area beneath the first membership function 808 may represent a set of values within first fuzzy set 804. Although first range of values 812 is illustrated for clarity in this exemplary depiction as a range on a single number line or axis, first range of values 812 may be defined on two or more dimensions, representing, for instance, a Cartesian product between a plurality of ranges, curves, axes, spaces, dimensions, or the like. First membership function 808 may include any suitable function mapping first range 812 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 8, first fuzzy set 804 may represent any value or combination of values as described above, including output from one or more algorithms, one or more machine-learning models, one or more sensors, and a predetermined class, such as without limitation a speech pattern, eye pattern, and/or cognitive status. A second fuzzy set 816, which may represent any value which may be represented by first fuzzy set 804, may be defined by a second membership function 820 on a second range 824; second range 824 may be identical and/or overlap with first range 812 and/or may be combined with first range via Cartesian product or the like to generate a mapping permitting evaluation overlap of first fuzzy set 804 and second fuzzy set 816. Where first fuzzy set 804 and second fuzzy set 816 have a region 828 that overlaps, first membership function 808 and second membership function 820 may intersect at a point 832 representing a probability, as defined on probability interval, of a match between first fuzzy set 804 and second fuzzy set 816. Alternatively or additionally, a single value of first and/or second fuzzy set may be located at a locus 836 on first range 812 and/or second range 824, where a probability of membership may be taken by evaluation of first membership function 808 and/or second membership function 820 at that range point. A probability at 828 and/or 832 may be compared to a threshold 840 to determine whether a positive match is indicated. Threshold 840 may, in a non-limiting example, represent a degree of match between first fuzzy set 804 and second fuzzy set 816, and/or single values therein with each other or with either set, which is sufficient for purposes of the matching process; for instance, threshold may indicate a sufficient degree of overlap between an output from one or more machine-learning models and/or sensors and a predetermined class, such as without limitation a cognitive state, for combination to occur as described above. Alternatively or additionally, each threshold may be tuned by a machine-learning and/or statistical process, for instance and without limitation as described in further detail below.

Further referring to FIG. 8, in an embodiment, a degree of match between fuzzy sets may be used to classify one or more of at least an eye pattern and at least a speech pattern to a cognitive status. For instance, if one or more of at least an eye pattern and at least a speech pattern has a fuzzy set matching a cognitive status fuzzy set by having a degree of overlap exceeding a threshold, processor 104 may classify the one or more of at least an eye pattern and at least a speech pattern as belonging to the cognitive status. Where multiple fuzzy matches are performed, degrees of match for each respective fuzzy set may be computed and aggregated through, for instance, addition, averaging, or the like, to determine an overall degree of match.

Still referring to FIG. 8, in an embodiment, one or more of at least an eye pattern and at least a speech pattern may be compared to multiple cognitive status fuzzy sets. For instance, one or more of at least an eye pattern and at least a speech pattern may be represented by a fuzzy set that is compared to each of the multiple cognitive status fuzzy sets; and a degree of overlap exceeding a threshold between the one or more of at least an eye pattern and the at least a speech pattern and any of the multiple cognitive status fuzzy sets may cause processor 104 to classify the one or more of at least an eye pattern and at least a speech pattern as belonging to a cognitive status. For instance, in one embodiment there may be two cognitive status fuzzy sets, representing respectively unimpaired and impaired cognitive performance. Impaired cognitive status may have an impaired fuzzy set; unimpaired cognitive status may have an unimpaired fuzzy set; and one or more of at least an eye pattern and at least a speech pattern may have a pattern fuzzy set. Processor 104, for example, may compare a pattern fuzzy set with each of impaired fuzzy set and unimpaired fuzzy set, as described above, and classify one or more of at least an eye pattern and at least a speech pattern to either, both, or neither of impaired or unimpaired cognitive statuses. Machine-learning methods as described throughout may, in a non-limiting example, generate coefficients used in fuzzy set equations as described above, such as without limitation x, c, and σ of a Gaussian set as described above, as outputs of machine-learning methods. Likewise, one or more of at least an eye pattern, at least a speech pattern, at least an eye parameter, and at least a speech parameter may be used indirectly to determine a fuzzy set, as pattern fuzzy set may be derived from outputs of one or more machine-learning models and/or algorithms that take the aforementioned patterns and/or parameters as inputs.

Figure 9:
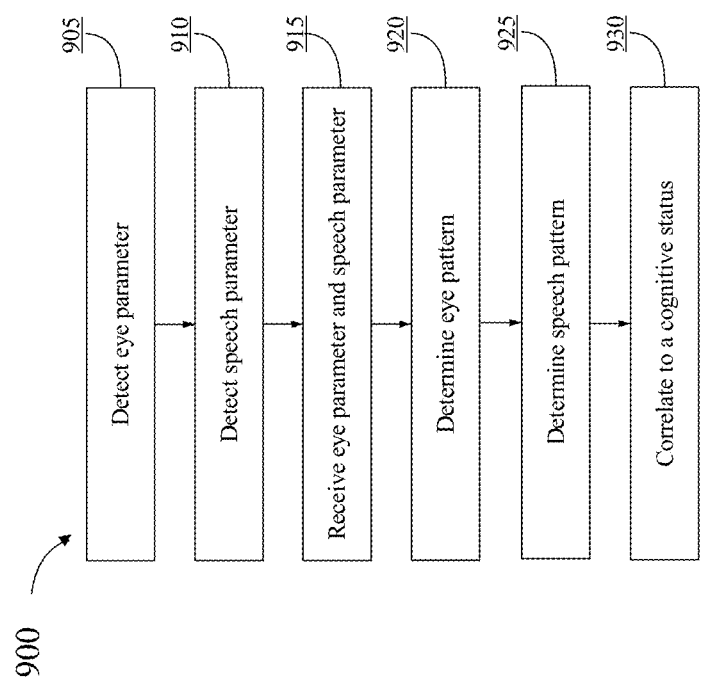
FIG. 9 is a flow diagram illustrating an exemplary method of determining actor status according to behavioral phenomena.

Referring now to FIG. 9, an exemplary method 900 of determining pilot status according to behavioral phenomenon is illustrated by way of a flow diagram. At step 905, method 900 may include detecting, using at least an eye sensor, at least an eye parameter as a function of at least an eye phenomenon. Eye sensor may include any sensor described in this disclosure, including with reference to FIGS. 1-8. Eye parameter may include any eye parameter described in this disclosure, including with reference to FIGS. 1-8. Eye phenomenon may include any eye phenomenon described in this disclosure, including with reference to FIGS. 1-8. In some embodiments, at least an eye sensor may include an electromyography sensor. In some cases, an electromyography sensor may be configured to detect at least an eye parameter as a function of at least an eye phenomenon. Electromyography sensor may include any electromyography sensor described in this disclosure, including with reference to FIGS. 1-8. In some embodiments, at least an eye sensor may include an optical sensor. In some cases, optical sensor may be configured to detect at least an eye parameter as a function of at least an eye phenomenon. Optical sensor may include any optical sensor described in this disclosure, including with reference to FIGS. 1-8.

With continued reference to FIG. 9, at step 910, method 900 may include detecting, using at least a speech sensor, at least a speech parameter as a function of at least a speech phenomenon. Speech sensor may include any sensor described in this disclosure, including with reference to FIGS. 1-8. Speech parameter may include any speech parameter described in this disclosure, including with reference to FIGS. 1-8. Speech phenomenon may include any speech phenomenon described in this disclosure, including with reference to FIGS. 1-8. In some embodiments, at least a speech sensor may include a bone conductance transducer. In some cases, bone conductance transducer may be configured to detect at least a speech parameter as a function of at least a speech phenomenon. Bone conductance transducer may include any bone conductance transducer described in this disclosure, including with reference to FIGS. 1-8. In some embodiments, at least a speech sensor may include a microphone. In some cases, microphone may be configured to detect at least a speech parameter as a function of at least a speech phenomenon. Microphone may include any microphone described in this disclosure, including with reference to FIGS. 1-8.

With continued reference to FIG. 9, at step 915, method 900 may include receiving, using a processor in communication with at least an eye sensor and at least a speech sensor, at least an eye parameter and at least a speech parameter. Processor may include any processor and/or computing device described in this disclosure, including with reference to FIGS. 1-8 and 10.

With continued reference to FIG. 9, at step 920, method 900 may include determining, using processor, at least an eye pattern as a function of at least an eye parameter. Eye pattern may include any eye pattern described in this disclosure, including with reference to FIGS. 1-8. In some embodiments, step 920 may additionally include receiving an eye pattern training data, inputting the eye pattern training data into an eye pattern machine learning algorithm, training an eye pattern machine learning model, as a function of the eye pattern machine learning algorithm, and determining the at least an eye pattern as a function of the eye pattern machine learning model and the at least an eye parameter. Eye pattern training data may include any training data described in this disclosure, including with reference to FIGS. 1-8. Eye pattern machine learning algorithm may include any machine learning algorithm described in this disclosure, including with reference to FIGS. 1-8. Eye pattern machine learning model may include any machine learning model described in this disclosure, including with reference to FIGS. 1-8.

With continued reference to FIG. 9, at step 925 method 900 may include determining, using processor, at least a speech pattern as a function of at least a speech parameter. Speech pattern may include any speech pattern described in this disclosure, including with reference to FIGS. 1-8. In some embodiments, step 925 may additionally include receiving a speech pattern training data, inputting the speech pattern training data into a speech pattern machine learning algorithm, training a speech pattern machine learning model, as a function of the speech pattern machine learning algorithm, and determining the at least a speech pattern as a function of the speech pattern machine learning model and at least a speech parameter. Speech pattern training data may include any training data described in this disclosure, including with reference to FIGS. 1-8. Speech pattern machine learning algorithm may include any machine learning algorithm described in this disclosure, including with reference to FIGS. 1-8. Speech pattern machine learning model may include any machine learning model described in this disclosure, including with reference to FIGS. 1-8.

With continued reference to FIG. 9, at step 930, method 900 may include correlating, using processor, one or more of at least an eye pattern and at least a speech pattern to a cognitive status. Cognitive status may include any cognitive status described in this disclosure, including with reference to FIGS. 1-8. In some embodiments, step 930 may additionally include receiving a cognitive status training data, inputting the cognitive status training data into a cognitive status machine learning algorithm, training a cognitive status machine learning model, as a function of the cognitive status machine learning algorithm, and determining the cognitive status as a function of the cognitive status machine learning model and one or more of the at least an eye pattern and the at least a speech pattern. Cognitive status training data may include any training data described in this disclosure, including with reference to FIGS. 1-8. Cognitive status machine learning algorithm may include any machine learning algorithm described in this disclosure, including with reference to FIGS. 1-8. Cognitive status machine learning model may include any machine learning model described in this disclosure, including with reference to FIGS. 1-8.

Still referring to FIG. 9, in some embodiments, method 900 may additionally include correlating, using processor, one or more of at least an eye parameter and at least a speech parameter to cognitive status.

Still referring to FIG. 9, in some embodiments, method 900 may additionally include determining, using processor, a confidence metric associated with correlation to cognitive status. Confidence metric may include any confidence metric described in this disclosure, including with reference to FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
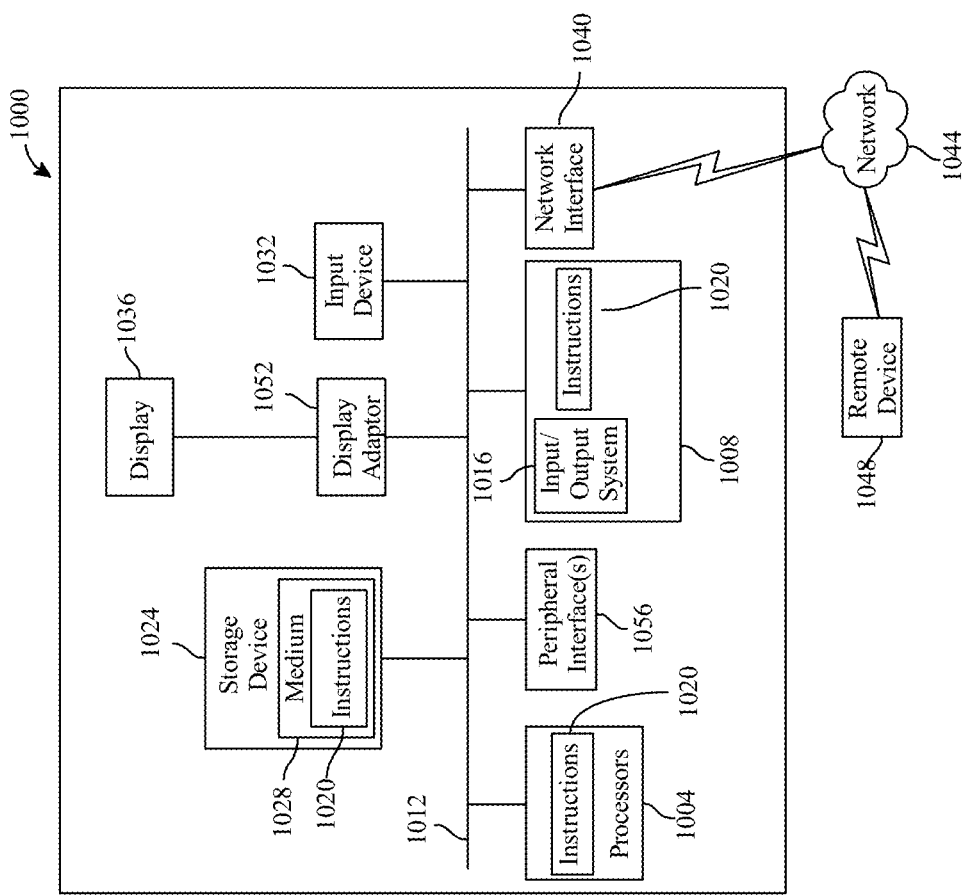
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIRE-WIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for determining actor status according to behavioral phenomenon, the system comprising:
   at least an eye sensor, wherein the at least an eye sensor is configured to detect an eye parameter;
   at least a physiological sensor, wherein the at least a physiological sensor is configured to detect a circulatory parameter; and
   a processor in communication with the at least an eye sensor and the at least a physiological sensor, wherein the processor is configured to:
      receive the eye parameter and the circulatory parameter;
      determine an eye pattern as a function of the eye parameter using an eye pattern machine learning process, wherein determining the eye pattern comprises:
         receiving historic eye pattern training data, which comprises eye parameter inputs correlated to eye patterns outputs; and
         training the eye pattern machine learning model as a function of the eye pattern training data; and
      correlate the eye pattern and the circulatory parameter to a cognitive status, wherein correlating the eye pattern and the circulatory parameter to the cognitive status comprises:
         receiving cognitive status training data comprising behavioral parameters correlated to a plurality of cognitive statuses, wherein the behavioral parameters comprise a plurality of circulatory parameters and a plurality of eye patterns;
         training a cognitive status machine learning model as a function of the cognitive status training data; and
         determining the cognitive status as a function of the cognitive status machine learning model, the eye pattern, and the circulatory parameter.

2. The system of claim 1, wherein the circulatory parameter comprises a blood oxygenation level.

3. The system of claim 2, wherein the at least a physiological sensor comprises at least an optical sensor configured to be located behind the ear of a user.

4. The system of claim 1, wherein the circulatory parameter comprises a pulse rate.

5. The system of claim 1, wherein the at least a physiological sensor comprises at least an optical sensor comprising a near-infrared spectroscopy sensor.

6. The system of claim 1, wherein the cognitive status is measured relative to a level of cognitive performance required for a given task.

7. The system of claim 1, wherein correlating the eye pattern and the circulatory parameter to the cognitive status further comprises compiling the cognitive status training data from historic information of a user.

8. The system of claim 1, wherein determining the eye pattern as a function of the eye parameter comprises:

receiving eye pattern training data, wherein the eye pattern training data correlates a plurality of eye parameters to a plurality of eye patterns;

training an eye pattern machine learning model using the eye pattern training data; and determining the at least an eye pattern using the eye pattern machine learning model.

9. The system of claim 1, wherein the processor is further configured to determine a confidence metric associated with the determination of the cognitive status.

10. The system of claim 1, wherein the processor is further configured to detect a physiological alarm condition as a function of the circulatory parameter.

11. A method for determining actor status according to behavioral phenomenon, the method comprising:

detecting, by at least an eye sensor, an eye parameter;

detecting, by at least a physiological sensor, a circulatory parameter;

receiving, by a processor, the eye parameter and the circulatory parameter;

determining, by the processor, an eye pattern as a function of the eye parameter, using an eye pattern machine learning process, wherein determining the eye pattern comprises:

receiving historic eye pattern training data, which comprises eye parameter inputs correlated to eye patterns outputs; and training the eye pattern machine learning model as a function of the eye pattern training data; and correlating, by the processor, the eye pattern and the circulatory parameter to a cognitive status, wherein correlating the eye pattern and the circulatory parameter to the cognitive status comprises:

receiving cognitive status training data comprising behavioral parameters correlated to a plurality of cognitive statuses, wherein the behavioral parameters comprise a plurality of circulatory parameters and a plurality of eye patterns;

training a cognitive status machine learning model as a function of the cognitive status training data; and determining the cognitive status as a function of the cognitive status machine learning model, the eye pattern, and the circulatory parameter.

12. The method of claim 11, wherein the circulatory parameter comprises a blood oxygenation level.

13. The method of claim 12, wherein the at least a physiological sensor comprises at least an optical sensor configured to be located behind the ear of a user.

14. The method of claim 11, wherein the circulatory parameter comprises a pulse rate.

15. The method of claim 11, wherein the at least a physiological sensor comprises at least an optical sensor comprising a near-infrared spectroscopy sensor.

16. The method of claim 11, wherein the cognitive status is measured relative to a level of cognitive performance required for a given task.

17. The method of claim 11, wherein correlating the eye pattern and the circulatory parameter to the cognitive status further comprises compiling the cognitive status training data from historic information of a user.

18. The method of claim 11, wherein determining the eye pattern as a function of the eye parameter comprises:

receiving eye pattern training data, wherein the eye pattern training data correlates a plurality of eye parameters to a plurality of eye patterns;

training an eye pattern machine learning model using the eye pattern training data; and determining the at least an eye pattern using the eye pattern machine learning model.

19. The method of claim 11, further comprising determining, by the processor, a confidence metric associated with the determination of the cognitive status.

20. The method of claim 11, further comprising detecting, by the processor, a physiological alarm condition as a function of the circulatory parameter.

* * * * *